(12) United States Patent
Pravda

(10) Patent No.: US 8,916,546 B2
(45) Date of Patent: *Dec. 23, 2014

(54) MATERIALS AND METHODS FOR TREATMENT AND DIAGNOSIS OF DISORDERS ASSOCIATED WITH OXIDATIVE STRESS

(75) Inventor: Jay Pravda, Palm Beach Gardens, FL (US)

(73) Assignee: Therapeutic Research LLC, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/298,106

(22) Filed: Nov. 16, 2011

(65) Prior Publication Data

US 2012/0077783 A1    Mar. 29, 2012

Related U.S. Application Data

(63) Continuation-in-part of application No. 12/664,237, filed as application No. PCT/US2008/007401 on Jun. 13, 2008, application No. 13/298,106, which is a continuation-in-part of application No. 11/540,864, filed on Sep. 28, 2006, now abandoned, and a continuation-in-part of application No. 11/107,179, filed on Apr. 15, 2005, now abandoned, and a continuation-in-part of application No. 10/927,742, filed on Aug. 27, 2004, now Pat. No. 7,312,243.

(60) Provisional application No. 61/414,047, filed on Nov. 16, 2010, provisional application No. 61/063,745, filed on Feb. 6, 2008, provisional application No. 60/934,505, filed on Jun. 13, 2007, provisional application No. 60/499,152, filed on Aug. 29, 2003.

(51) Int. Cl.
| | |
|---|---|
| *A61K 31/606* | (2006.01) |
| *A61P 1/04* | (2006.01) |
| *A61K 31/385* | (2006.01) |
| *A61K 31/616* | (2006.01) |
| *A61K 45/06* | (2006.01) |
| *A61K 9/00* | (2006.01) |
| *A61K 9/10* | (2006.01) |
| *A61K 9/48* | (2006.01) |

(52) U.S. Cl.
CPC ............ *A61K 31/385* (2013.01); *A61K 31/616* (2013.01); *A61K 45/06* (2013.01); *A61K 9/0031* (2013.01); *A61K 9/10* (2013.01); *A61K 9/48* (2013.01)
USPC ............................................................. 514/183

(58) Field of Classification Search
CPC .................................................. A61K 31/607
USPC ......................................................... 514/183
See application file for complete search history.

(56) References Cited

U.S. PATENT DOCUMENTS

| | | | |
|---|---|---|---|
| 4,657,900 | A | 4/1987 | Powell |
| 4,980,173 | A | 12/1990 | Halskov |
| 5,082,651 | A | 1/1992 | Healey |
| 5,084,481 | A | 1/1992 | Ulrich et al. |
| 5,378,470 | A | 1/1995 | Lahr |
| 5,563,131 | A | 10/1996 | Berliner et al. |
| 5,569,670 | A | 10/1996 | Weischer et al. |
| 5,728,735 | A | 3/1998 | Ulrich et al. |
| 5,817,630 | A | 10/1998 | Hofmann et al. |
| 5,945,127 | A | 8/1999 | Breitenbach et al. |
| 6,197,749 | B1 | 3/2001 | Hamuro et al. |
| 6,262,019 | B1 | 7/2001 | Keller et al. |
| 6,444,221 | B1 | 9/2002 | Shapiro et al. |
| 6,605,637 | B1 | 8/2003 | Harnett et al. |
| 6,664,287 | B2 | 12/2003 | Avery et al. |
| 6,887,894 | B2 | 5/2005 | Krämer et al. |
| 7,157,444 | B2 | 1/2007 | Nelson |
| 2005/0090553 | A1 | 4/2005 | Shapiro |
| 2005/0260140 | A1 | 11/2005 | White et al. |
| 2006/0264408 | A1* | 11/2006 | Haj-Yehia ................... 514/150 |
| 2007/0269379 | A1* | 11/2007 | Mitragotri et al. ............ 424/9.2 |
| 2008/0107650 | A1* | 5/2008 | Tartaglia et al. ........... 424/133.1 |
| 2008/0234380 | A1 | 9/2008 | Shapiro |
| 2009/0181081 | A1 | 7/2009 | Gojon-Romanillos |
| 2010/0112088 | A1 | 5/2010 | Pravda |

FOREIGN PATENT DOCUMENTS

| | | |
|---|---|---|
| CA | 2097732 | 12/2002 |
| EP | 0671168 | 5/2000 |
| WO | WO/00/59899 | 10/2000 |
| WO | 2002089796 | 11/2002 |
| WO | WO2004/071496 A1 | 8/2004 |

OTHER PUBLICATIONS

R H Grace, A E Gent, and M D Hellier, Comparative trial of sodium cromoglycate enemas with prednisolone enemas in the treatment of ulcerative colitis, Gut, 1987, 28, 88-92.*

Scheppach et al., Effect of Butyrate Enemas on the Colonic Mucosa in Distal Ulcerative Colitis, Gastroenterology 1992;103:51-56.*

Christl, S.U. et al. "Antagonistic effects of sulfide and butyrate on proliferation of colopic mucosa a potential role for these agents in the pathogenesis of ulcerative colitis", *Digestive diseases and sciences*, 1997, 41(12):2477-81, abstract only.

(Continued)

*Primary Examiner* — Kendra D Carter
*Assistant Examiner* — Jason A Deck
(74) *Attorney, Agent, or Firm* — Lucas & Mercanti, LLP

(57) ABSTRACT

The subject invention pertains to materials and methods for the prevention and treatment of disease conditions associated with oxidative stress or a compromised reducing environment, including inflammatory bowel diseases such as Crohn's disease and ulcerative colitis. Another aspect of the subject invention concerns compositions formulated for administration as an enema. The subject invention also concerns compositions formulated for oral administration. Methods of the invention include administration of compounds or compositions of the invention. In one embodiment, compounds or compositions of the invention are rectally instilled in a patient. In another embodiment, compounds or compositions are orally administered.

15 Claims, 3 Drawing Sheets

(56) References Cited

OTHER PUBLICATIONS

Kolgazi, Meltem et al. "α-Lipoic acid modulates gut inflammation induced by trinitrobenzene sulfonic acid in rats", *Journal of Gatroenterology and Hepatology*, 2007, 22:1859-1865.

Pravda, Jay "Radical induction therapy of ulcerative colitis", *World Journal of Gastroenterology*, 2005, 11(16):2371-2384.

Santhanam, Srikanth et al. "Impairment of mitochondrial acetoacetyl CoA thiolase activity in the colonic mucose of patients with ulcerative colitis", *Free Radical Research Communications*, 1993, 18(2):115-122, abstract only.

Sehirli, O et al. "Antioxidant effect of alpha-lipoic acid against ethanol-induced gastric mucosal erosion in rats", *Pharmacology*, 2008, 81(2):173-180.

Suzuki, YJ et al. "Antioxidant activities of dihydrolipoic acid and its structural homologues", *Free Radical Research Comm.*, 1993, 18(2):115-122, abstract only.

Abraham, N. et al. "Is smoking an indirect risk factor for the development of ulcerative colitis? An age- and sex-matched case-control study" *Journal of Gastroenterology and Hepatology*, 2003, pp. 139-146, vol. 18, No. 2.

Allison, M. C. et al. "Prevalence of proximal fecal stasis in active ulcerative colitis" *Gut*, 1991, pp. 179-182, vol. 32, No. 2.

AW, T. Y. "Molecular and cellular responses to oxidative stress and changes in oxidation-reduction Imbalance in the intestine" *Am. J. Clin. Nutr.*, 1999, pp. 557-565, vol. 70.

Bagchi, D. et al. "Stress, Diet and Alcohol-induced Oxidative Gastrointestinal Mucosal Injury in Rats and Portection by Bismuth Subsailoylate" *J. Appl. Toxicol.*, 1998, pp. 3-13, vol. 18, No. 1.

Bailey, S. M. et al, "Ethanol Stimulate the Production of Reactive Oxygen Species at Mitochandrial Complexes I and III", *Free Radical Biology and Medicine*, 1999, pp. 891-900, vol. 27, Nos. 7-8.

Basit, A. et al. "Perspectives on Colonic Drug Delivery", *Pharmatech*, 2003, pp. 185-190, ed. Business Briefings Ltd., London, England.

Batist, G. et al. "Interindividual variation in phase II detoxification enzymes in normal human colon mucosa" *Biochemical Pharmacology*, 1988, pp. 4241-4243, vol. 37, No. 21.

Beaugerie, L. et al. "Impact of Cessation of Smoking on the Course of Ulcerative Colitis" *The American Journal of Gastroenterology*, 2001, pp. 2113-2116, vol. 96, No. 7.

Benson, K. W. et al. "Fecal Impaction" *Am. J. M. Sc.*, 1939, pp. 541-545, vol. 198.

Bertz, R. J. et al. "Use of In-Vitro and In-Vivo Data to Estimate the Likelihood of Metabolic Pharmacokinetic Interactions" *Clinical Pharmacokinetics*, Mar. 1997, pp. 210-258, vol. 32, No. 3.

Bilotta, J.J. et al. "Hydrogen peroxide enteritis: the 'snow white'sign" *Gastrointestinal Endoscopy*, Sep.-Oct. 1989, pp. 428-430, vol. 35, No. 5.

Black, D. A. et al. "Transit Time in Ulcerative Colitis" *Scand J. Gastroenterol*, 1987, pp. 872-876, vol. 22.

Blau, S. et al. "Differences in the reducing power along the rat GI tract: Lower antioxidant capacity of the colon" *Molecular and Cellular Biochemistry*, 1999, pp. 185-191, vol. 194.

Blaut, M. "Assessment of bacteria in the gut microbial ecosystem" in *Intestinal flora, European Concerted Action*, Chapter 2, 2000, pp. 1-3.

Boveris, A. et al. "The Cellular Production of Hydrogen Peroxide" *Biochem. J.*, 1972, pp. 617-630, vol. 128.

Boveris, A. et al. "The Mitochondrial Generation of Hydrogen Peroxide" *Biochem. J.*, 1973, pp. 707-716, vol. 134.

Boveris, A. et al. "Mitochondrial Production of Hydrogen Peroxide Regulation by Nitric Oxide and the Role of Ubisemiquinone" *Life*, 2000, pp. 245-250, vol. 50.

Brunner, L. S. et al. "Perioperative Management of the Surgical Patient" In *Textbook of Medical Surgical Nursing*, 4th edition, 1980, p. 358, Lippincott, Philadelphia.

Buetler, E. et al. "Ethnic Variation in Red Cell giutalhione Peroxidase activity" *Blood*, Jul. 1975, pp. 103-110, vol. 46, No. 1.

Cadenas, E. et al. "Mitochondrial Free Radical Generation, Oxidative Stress, and Aging" *Free Radical Biology & Medicine*, 2000, pp. 222-230, vol. 29, Nos. 3-4.

Caprari, P. et al. "6-Phosphogluconate dehydrogenase deficiency in an Italian family" *Ann. Hemetol.*, 2001, pp. 41-44, vol. 80.

Carpenter, H. A. et al. "The Importance of Clinicopathological Correlation in the Diagnosis of Inflammatory Conditions of the Colon: Histological Patterns With Clinical implications" *The American Journal of Gastroenterology*, 2000, pp. 878-896, vol. 95, No. 4.

Chance, B. et al. "Hydroperoxide Metabolism in Mammalian Organs", *Physiological Reviews*, Jul. 1979, pp. 527-605, vol. 59, No. 3.

Chen, N. et al. "Physiologic concentrations of homocysteine inhibit the human plasma GSH peroxidase that reduces organic hydroperoxides" *J. Lab. Clin. Med.*, 2000, pp. 58-65, vol. 136, No. 1.

Chen, S. et al. "Hydroxl-radical production in physiological reactions—A novel function of peroxidase" *Eur. J. Biochem.*, 1999, pp. 726-735, vol. 260, No. 3.

Ciftci, M. et al. "Effects of Some Drugs on Rat Erythrocyte 6-Phosphogluconate Dehydrogenase: An In Vitro and In Vivo Study" *Polish Journal of Pharmacology*, 2002, pp. 275-280, vol. 54.

Cho, J. H. et al. "Identification of novel susceptibility loci for inflammatory bowel disease on chromosomes 1p, 3q, 4q; Evidence for epistasis between 1p and IBD1" *Proc. Natl. Acad. Sci. USA*, Jun. 1998, pp. 7502-7507, vol. 95.

Cho, J. H. et al. "Linkage and linkage disequilibrium in chromosome band 1p36 in American Chaldeans with inflammatory bowel disease" *Human Molecular Genetics*, 2000, pp. 1425-1432, vol. 9, No. 9.

Dalekos G. N. et al. "Zinc, copper and immunological markers in the circulation of well nourished patients with ulcerative colitis" *Eur. J. Gastroenterol Hepatol.*, Apr. 1998, pp. 331-337, vol. 10, No. 4, abstract only.

Davidson, R. G. "Electrophorelic variants of human 6-phosphogluconate dehydrogenase: population and family studies and description of a new variant" *Ann. Hum. Genet.*, 1967, pp. 355-361, vol. 30.

Davies, K. J. A. "Oxidative Stress, Antioxidant Defenses, and Damage Removal, Repair, and Replacement Systems" *Life*, 2000, pp. 279-289, vol. 50.

Dern, R. J. et al. "Hereditary variation of erythrocytic 6-phosphogluconate dehydrogenase" *J. Lab. & Clin. Med.*, Feb. 1966, pp. 255-264, vol. 67, No. 2.

Drossman, D. et al. "Rome II: the functional gastrointestinal disorders : diagnosis, pathophysiology, and treatment : a multinational consensus" In *The Functional Gastrointestinal Disorders*, eds, Douglas A. Dross, Enrico Corazzlari, 2000, Library of Congress Catloging-in-Publication Data.

Drossman, D. A. et al. "U.S. Householder Survey of Functional Gastrointestinal Disorders. Prevalence, Soclodemography, and Health Impact" *Digestive Diseases and Sciences*, Sep. 1993, pp. 1569-1580, vol. 38, No. 9.

Duncan, G. G. "Folic Acid (Folacin)" In *Diseases of Metabolism—Detailed Methods of Diagnosis and Treatment*, 5th edition, 1964, pp. 614-618, W. B. Saunders Company, Philadelphia and London.

Eaton, J. W. et al. "Acatalasemia" In *The Metabolic & Molecular Bases of Inherited Disease*, 7th edition, Chapter 74, eds., Scriver C. R. et al., 1995, pp. 2371-2379, McGraw-Hill Medical Publishing Division.

Eaton, J. W. et al. "Molecular Bases of Cellular Iron Toxicity" *Free Radical Biology & Medicine*, 2002, pp. 833-840, vol. 32, No. 2.

Eberhardt M. K. In *Reactive Oxygen Metabolites—Chemistry and Medical Consequences*, 2001, pp. 23, 51, 63, 64, 81, 118, 125, and 262, CRC Press.

Elsborg, L. et al. "Folate Deficiency in Chronic Inflammatory Bowel Diseases" *Scand. J. Gastroent.*, 1979, pp. 1019-1024, vol. 14, No. 8.

Everhart, J. E. et al. "A Longitudinal Survey of Self-Reported Bowel Habits in the United States" *digestive Diseases and Sciences*, Aug. 1989, pp. 1153-1162, vol. 34, No. 8.

Everson, C. A. et al. "Systemic bacterial invasion induced by sleep deprivation" *Am. J. Physiol. Regulatory Integrative Comp. Physiol.* 2000, pp. R905-R916, vol. 278.

Farrell, R. J. et al. "Ulcerative colitis" *The Lancet*, Jan. 26, 2002, pp. 331-340, vol. 359.

(56) References Cited

OTHER PUBLICATIONS

Farrokhar, F. et al. "A Critical Review of Epidermiological Studies In Inflammatory Bowel Disease" *Scand. J. Gastroenterol*, 2001, pp. 2-15, vol. 36, No. 1.
Fernandez-Banares, F. et al. "Vitamin Status In Patients with Inflammatory Bowel Disease" *The American Journal of Gastroenterology*, 1989, pp. 744-748, vol. 84, No. 7.
Fowler, J. S. et al. "Monoamine Oxidase and Cigarette Smoking" *Neuro Toxicology*, 2003, pp. 75-82, vol. 24, No. 1.
Fridovich, L. "Oxygen Toxicity: A Radical Explanation" *The Journal of Experimental Biology*, 1998, pp. 1203-1209, vol. 201.
Friedman, G. et al. "A Common Mutation A1298C in Human Methylenetetrahydroloiate Reductase Gene: Association with Plasma Gene: Associastion with Plasma Total Homocysteine and Folate Concentrations" *J. Nutr.*, 1999, pp. 1656-1661, vol. 129, No. 9.
Geerling, B. J. et al. "Diet as a Risk Factor for the Development of Ulcerative Colitis" *The American Journal of Gastroenterology*, Apr. 2000, pp. 1008-1013, vol. 95, No. 4.
Goglia, F. et al. "Thyroid Hormones and Mitochondria" *Bioscience Reports*, Feb. 2002, pp. 17-29, vol. 22, No. 1.
Gordillo, E. et al. "Implication of Lysine Residues in the Loss of 6-Phosphogluconate Dehydrogenase Activity in Aging Human Erythrocytes" *Mechanisms of Ageing and Development*, 1991, pp. 291-297, vol. 59, No. 3.
Goyette, P. et al. "Gene structure of human and mouse methylenetetrahydrofolate reductase (MTHFR)" *Mammallan Genome*, 1998, pp. 652-656, vol. 9.
Graf, E. et al. "Iron-catalyzed Hydroxyl Radical Formation Stringent Requirement for Free Iron Coordination Site" *The Journal of Biological Chemistry*, Mar. 25, 1984, pp. 3620-3624, vol. 259, No. 6.
Granger, D. N. et al. "Role of Oxygen Radicals in the Pathogenesis of Intestinal Ischemia" *The Physiologist*, 1983, pp. 159-164, vol. 26, No. 3.
Grisham, M. B. et al. "Oxidant Defense Mechanisms in the Human Colon" *Inflammation*, 1990, pp. 669-680, vol. 14, No. 6.
Gulati, S. et al. "Alterations of peroxisomal function in ischemia-reperfusion injury of rat kidney" *Biochimica et Biophysica Acta*, 1993, pp. 291-298, vol. 1182, No. 3.
Guyton, A. C. et al. "Functional Organization of the Human Body and Control of the 'Internal Environment'" In *Human Physiology and Mechanisms of Disease*, 6th edition, Chapter 1, 1997, p. 3, W. B. Saunders Company.
Han, D. et al. "Mitochondrial respiratory chain-dependent generation of superoxide anion and its release into the intermembrane space" *Biochem. J.*, 2001, pp. 411-416, vol. 353.
Harris, M. L. et al. "Free Radicals and Other Reactive Oxygen Metabolites in Inflammatory Bowel Disease: Cause, Consequence or Epiphenomenon?" *Pharmac. Ther.*, 1992, pp. 375-408, vol. 53.
Hendrickson, B. A. et al. "Clinical Aspects and Pathophysiology of Inflammatory Bowel Disease" *Clinical Microbiology Reviews*, Jan. 2002, pp. 79-94, vol. 15, No. 1.
Hoek, J. B. et al. "Alcohol and Mitochondria: A Dysfunctional Relationship" *Gastroenterology*, 2002, pp. 2049-2063, vol. 122.
Huycke, M. M. et al. "Extracellular superoxide production by *Enterococcus faecalls* requires demethylmenaquinone and is attenuated by functional terminal quinol oxidases" *Molecular Microbiology*, 2001, pp. 729-740, vol. 42, No. 3.
Huycke, M. M. et al. "Enterococcus faecalls produces extracellular superoxide and hydrogen peroxide that damages colonic epithelial cell DNA", *Carcinogenesis*, 2002, pp. 529-536, vol. 23, No. 3.
Huycke, M. M. et al. "In Vivo Production of Hydroxyl Radical by *Enterococcus faecalis* Colonizing the Intestinal Tract Using Aromatic Hydroxylation" *Free Radical & Medicine*, 2002, pp. 818-826, vol. 33, No. 6.
Isman, C. A. et al. "Methimazole-Induced hypothyroldism in rats amellorates oxidative injury in experimental colitis" *Journal of Endocrinology*, 2003, pp. 471-476, vol. 177.
Jarnerot, G. et al. "The Thyroid in Ulcerative Colitis and Crohn's Disease" *Acta Med. Scand.*, 1975, pp. 83-87, vol. 197.
Karlinger, K. et al. "The epidemiology and the pathogenesis of inflammatory bowel disease" *Eur. J. Radiol.*, Sep. 2000, pp. 154-167, vol. 35, No. 3.
Kawai, M. et al. "A case of ulcerative colitis induced by oral ferrous sulfate" *Acta Paediatr. Jpn.*, Aug. 1992, pp. 476-478, vol. 34, No. 4, abstract only.
Kehrer, J. P. "The Haber-Weiss Reaction and Mechanisms of Toxicity" *Toxicology*, 2000, pp. 43-50, vol. 149.
Keyer, K. et al. "Superoxide accelerates DNA damage by elevating free-iron levels" *Proc. Natl. Acad. Sci. USA*, Nov. 1996, pp. 13635-13640, vol. 93.
Koutroubakis, I. E. et al. "Hyperhomocysteinernia in Greek Patients with Inflammatory Bowel Disease" *Digestive Diseases and Sciences*, Dec. 2000, pp. 2347-2351, vol. 45, No. 12.
Larsson, A. et al. "Glutathione Synthetase Deficiency and Other Disorders of the γ-Glutamyl Cycle" In *The Metabolic & Molecular Bases of Inherited Disease*, 8th edition, Chapter 96, ed. Scriver et al., 2001, pp. 2205-2215, McGraw-Hill Medical Publishing Division.
Lechin, F. et al. "Stress Versus Depression" *Prog. Neuro-Psychopharmacol & Biol. Psychiat.*, 1996, pp. 899-950, vol. 20.
Li, C. et al. "Reactive species mechanisms of cellular hypoxia-reoxygenation injury" *Am. J. Physiol. Cell Physiol.*, 2002, pp. C227-C241, vol. 282.
Liochev, S. I. et al. "Superoxide and Iron: Partners in Crime" *Life*, 1999, pp. 157-161, vol. 48.
Liu, S-S. "Generating, Partitioning, Targeting and Functioning of Superoxide in Mitochondria" *Bioscience Reports*, 1997, pp. 259-272, vol. 17, No. 3.
Madretsma, S. et al. "In-vivo effect of nicoting on cytokine production by human non-adherent mononuclear cells" *Eur. J. Gastroenterol. Hepatol.*, Oct. 1996, pp. 1017-1020, vol. 8, No. 10, abstract only.
Mahmud, N. et al. "Increased prevalence of methylenetetrahydrofolate reductase C677T variant in patients with inflammatory bowel disease and its clinical implications" *Gut*, 1999, pp. 389-394, vol. 45.
Maier, B. R. et al. "Effects of a high-beef diet on bowel flora: a preliminary report" *The American Journal of Clinical Nutrition*, Dec. 1974, pp. 1470-1474, vol. 27.
"Management of Ulcerative Colitis" *National Guideline Clearinghouse*: http://www.ngc.gov, 2001, pp. 1-10.
Meyer, C. T. et al. "Hydrogen Peroxide Colitis: A Report of Three Patients" *J. Clin. Gastroenterol.*, 1981, pp. 31-35, vol. 3.
Meyers, S. et al. "The "Natural History" of Ulcerative Colitis: An Analysis of the Placebo Response" *J. Clin. Gastroenterol.*, 1989, pp. 33-37, vol. 11, No. 1.
Millar, A. D. et al. "Effects of iron and iron chelation in vitro on mucosat oxidant activity in ulcerative colitis" *Aliment Pharmacol. Ther.*, 2000, pp. 1163-1168, vol. 14.
*Mitochondria in Pathogenesis*, ed. by Lemasters, J. et al., 2001, pp. 281-284, 286, Kluwer Academic/Plenum Publishers.
*The Metabolic & Molecular Bases of Inherited Disease*, 8th edition, Chapter 155, eds. Scriver, C. R. et al., 2001, pp. 3897-3993, vol. 3, McGraw-Hill Medical Publishing Division.
*The Metabolic & Molecular Bases of Inherited Disease*, 8th edition, Chapter 182, eds. Scriver, C. R. et al., 2001, pp. 4650-4651, McGraw-Hill Medical Publishing Division.
Modebe, O. "Autoimmune thyroid disease with ulcerative colitis" *Postgraduate Medical Journal*, 1986, pp. 475-476, vol. 62.
Nelson, M. S. "Biochemical and Genetic Characterization of the Lowell Variant: A New Phenotype of 6-Phosphogluconate Dehydrogenase" *Human Genetics*, 1982, pp. 333-336, vol. 62.
"Nicotine Pharmacology" In *Cleaning the Smoke: Assessing the Science Base for Tobacco Harm Reduction*, Chapter 9, 2001, pp. 243, 267.
Odes, H. S. et al. "Effects of Current Cigarette Smoking on Clinical Course of Crohn's Disease and Ulcerative Colitis" *Digestive Diseases and Sciences*, Aug. 2001, pp. 1717-1721, vol. 46, No. 8.
O'Donnell, V. B. et al. "High rates of extracellular superoxide generation by cultured human fibroblasts: involvement of a lipid-metabolizing enzyem" *Biochem. J.*, 1996, pp. 805-812, vol. 318.

(56) References Cited

OTHER PUBLICATIONS

Oren, R. et al. "Anti-thyroid drugs decrease mucosal damage in a rat model of expereimental colitis" *Aliment Pharmacol. Ther.*, 1997, pp. 341-345, vol. 11, No. 2.

Outinen, P. A. et al. "Homocysteine-Induced Endoplasmic Reticulum Stress and Growth Arrest Leads to Specific Changes in Gene Expression in Human Vascular Endothelial Cells" *Blood*, Aug. 1, 1999, pp. 959-967, vol. 94, No. 3.

Ouyang, Y. et al. "Suppression of human IL-1β, IL-2, IFN-γ and TNF-αproduction by cigarette smoke extracts" *J. Allergy Clin. Immunology*, 2000, pp. 280-287, vol. 106, No. 2.

Owen, R. W. et al. "Generation of reactive oxygen species by the faecal matrix" *Gut*, 2000, pp. 225-232, vol. 46.

Parks, D. A. et al. "Oxygen radicals: effects on intestinal vascular permeability" *Gastrointest. Liver Physiol.*, 1984, pp. G167-G170, vol. 10.

Parks, D. A. et al. "Contributions of ischemia and reperfusion to mucosal lesion formation" *Gastrointest. Liver Physiol.*, 1986, pp. G749-G753, vol. 13.

Parr, C. W. "Erythrocyte Phosphogluconate Dehydrogenase Polymorphism" *Nature*, Apr. 30, 1966, pp. 487-489, vol. 210, No. 5035.

Parr, C. W. et al. "Inherited quantitative variations of human phosphogluconate dehydrogenase" *Ann. Hum. Genet.*, 1967, pp. 339-352, vol. 30, No. 4.

Pryor, W. A. et al. "The Inhibitory Effect of Extracts of Cigarette Tar on Election Transport of Mitochondria and Submitochondrial Particles" *Free Radical Biology and Medicine*, 1992, pp. 365-372, vol. 12.

Pumphrey, R. E. "Hydrogen Peroxide Proctitis" *American Journal of Surgery*, Jan. 1951, pp. 60-62, vol. 81.

Rady, P.L. et al. "Methylenetetrahydrofolate Reductase (MTHFR): The Incidence of Mutations C677T and A1298C in the Ashkenazi Jewish Population" *American Journal of Medical Genetics*, 1999, pp. 380-384, vol. 86, No. 4.

Rao, S. S. C. et al. "Symptoms and stool patterns in patients with ulcerative colitis" *Gut*, 1988, pp. 342-345, vol. 29.

Reifen, R. et al. "Iron Supplementation May Aggravate Inflammatory Status of Colitis in a Rat Model" *Digestive Diseases and Sciences*, Feb. 2000, pp. 394-397, vol. 45, No. 2.

Ringstad, J. et al. "Serum Selenium, Copper, and Zinc Concentrations in Crohn's Disease and Ulcerative Colitis" *Scand. J. Gastroenterol.*, 1993, pp. 605-608, vol. 28, No. 7.

Roediger, W. et al. "Metabolic induction of experimental ulcerative colitis by inhibition of fatty acid oxidation" *Br. J. exp. Pathology*, 1986, pp. 773-782, vol. 67.

Roediger, W. et al. "Human Colonocyte Detoxification" *Gut*, 1997, pp. 731-734, vol. 41, No. B.

Roth, M-P, et al. "Geographic Origins of Jewish Patients With Inflammatory Bowel Disease" *Gastroenterology*, 1989, pp. 900-904, vol. 97, No. 4.

Schultz, B. E. et al. "Structures and Proton-Pumping Strategies of Mitochondrial Respiratory Enzymes" *Annu. Rev. Biophys. Biomol. Struct.*, 2001, pp. 23-65, vol. 30.

Schwartz, E. et al. "Letter to the editor, Hydrogen Peroxide Injury to the Colon" *Digestive Diseases and Sciences*, Jun. 1995, pp. 1290-1291, vol. 40, No. 6.

Shaw, A. et al. "Gas Embolism Produced by Hydrogen Peroxide" *The New England Journal of Medicine*, Aug. 3, 1967, pp. 238-241, vol. 277, No. 5.

Sheehan, J. F. et al. "Ulcerative Colitis Following Hydrogen Peroxide Enema: Case Report and Experimental Production with Transient Emphysema of Colonic Wall and Gas Embolism" *Laboratory Investigation*, 1960, pp. 150-168, vol. 9, No. 1.

Soderholm, J. D. et al. "Chronic Stress Induces Mast Cell-Dependent Bacterial Adherence and Initiates Mucosal Inflammation in Rat Intestine" *Gastroenterology*, 2002, pp. 1099-1108, vol. 123.

Soderholm, J. D. et al. "Stress and the Gastrointestinal Tract II. Stress and intestinal barrier function" *Am. J. Physiol. Gastrointest. Liver Physiol.*, 2001, pp. G7-G13, vol. 280.

Souchard, J. P. et al. "Electron spin resonance detection of extracellular superoxide anlon releases by cultured endothelial cells" *Free Radic. Res.*, Nov. 1998, pp. 441-449, vol. 29, No. 5, abstract only.

Srigiriohar, K. et al. "Oral repletion of iron induces free radical mediated alterations in the gastrointestinal tract of rat" *Molecular and Cellular Biochemistry*, 2001, pp. 91-98, vol. 219, Nos. 1-2.

St-Pierre, J. et al. "Topology of Superoxide Production from Different Sites in the Mitochondrial Electron Transport Chain" *The Journal of Biological Chemistry*, Nov. 22, 2002, pp. 44784-44790, vol. 277, No. 47.

Thibaud, D. et al. "Rectal bleeding: complication of hydrogen peroxide enemas" *Archives de pediatrie : organe officiel de la Societo franceise de pediatrie.*, 2001, pp. 1267-1268, vol. 8, No. 11.

Tomlinson, J. E. et al. "Repression of Pentose Phosphate Pathway Dehydrogenase Synthesis and mRNA by Dietary Fat in Rats" *American Institute of Nutrition*, 1988, pp. 408-415, vol. 118, No. 3.

Topping D. L. et al. "Short-Chain Fatty Acids and Human Colonic Function: Roles of Resistant Starch and Nonstarch Polysaccharides" *Physiological Reviews*, Jul. 2001, pp. 1031-1064, vol. 81, No. 3.

Torisu, T. et al. "A Rare Case of Ulcerative Colitis Complicating Wilson's Disease. Possible Association between the Two Diseases" *J. Clin. Gastroenetrol.*, 2002, pp. 43-45, vol. 35, No. 1.

Turrens, J. F. "Superoxide Production by the Mitochondrial Respiratory Chain" *Bioscience Reports*, 1997, pp. 3-8, vol. 17, No. 1.

Upchurch, G. R. et al. "Homocyst(e)ine Decreases Bioavailable Nitric Oxide by a Mechanism involving Glutathione Peroxide" *The Journal of Biological Chemistry*, Jul. 4, 1997, pp. 17012-17017, vol. 272, No. 27.

Van Vleet, T. R. et al. "Inhibition of Human Cyinchrome P450.2E1 by Nicotine, Cotinlne, and Aqueous Cigarette Tar Extract in Vitro" *Toxicological Sciences*, 2001, pp. 185-191, vol. 64.

Venditti, P. et al. "Effects of Thyroid State on $H_2O_2$ Production by Rat Heart Mitochondria: Sites of Production with Complex I- and Complex II-Linked Substrates" *Hormone Metabolic Research*, 2003, pp. 55-61, vol. 35.

Venditti, P. et al. "Effect of thyroid state on lipid peroxidation, antioxidant defences, and susceptibility to oxidative stress in rat tissues" *Journal of Endocrinology*, 1997, pp. 151-157, vol. 155.

Whelan, G. "Epiderniology of Inflammatory Bowel Disease" *Medical Clinics of North America*, Jan. 1990, pp. 1-12, vol. 74, No. 1.

Wilcken, D. E. L. et al. "Relationship Between Homocysteine and Superoxide Dismutase in Homocystinuria Possible Relevance to Cardiovascular Risk" *Arterioscler Thromb Vasc. Biol.*, May 2000, pp. 1199-1202, vol. 20.

Babior, B. M. et al. "The $O_2$ Producing Enzyme of Human Neutrophils" *Journal of Biological Chemistry*, Mar. 10, 1981, pp. 2321-2323, vol. 256, No. 5.

Rosenblatt, D. S. "Inherited Disorders of Folate and Cobalamin Transport and Metabolism" In *The Metabolic & Molecular Bases of Inherited Disease*, 8th edition, Chapter 155, eds, Scriver C. R. et al., 1995, pp. 3897-3910 and 3924-3933, McGraw-Hill Medical Publishing Division.

STN accession No. 94: 19076 Kondracki Dissertation Abstracts International, 1993, 54(12B) pp. 6208.

Van Den Worm, E., "Investigation on apocynin, a potent NADPH oxidase inhibitor" May 2001, title page and p. 75.

Praff, P., Weide, F., and Kuhn, R., "Investigation of Derivatization of Oligosaccharides by Means of Reductive Amination for Separation in Capillary Electrophoresis" *Chromatographia*, Jun. 12, 1999, pp. 666-670, vol. 49, No. 11/12.

Doussiere, J., and Vignais, P.V., "Diphenylene iodonium as an inhibitor of the NADPH oxidase complex of bovine neutrophils" *Eur. J. Biochem.*, 1992, pp. 61-71, vol. 208.

Kowaltowski, A.J. et al., "Reactive Oxygen Generation by Mitochondria" in *Mitochondria in Pathogenesis*, 2001, Chapter 14, eds. Lemasters J.J. et al., pp. 281-286, Kluwer Academic/Plenum Publishers.

(56) References Cited

OTHER PUBLICATIONS

International Search Report and Written Opinion issued in PCT/US2008/007401 and dated Dec. 26, 2008.

Mulder, C.J. et al., "Beclomethasone dipropionate (3 mg) versus 5-aminosalicylic acid (2 g) versus the combination of both (3 mg/2 g) as retention enemas in active ulcerative proctitis." Eur J Gastroenterol Hepatol. 8: 549-553, 1996.

Senagore, A.J. et al., "Short-chain fatty acid enemas: a cost-effective alternative in the treatment of nonspecific proctosigmoiditis." Dis Colon Rectum, 35: 923-927, 1992.

Manguso, F. at al., "Meta-analysis: the efficacy of rectal beclomethasone dipropionate vs. 5-aminosalicylic acid in mild to moderate ulcerative colitis." Aliment Pharmacol Ther. 26: 21-29, 2007.

Extended European Search Report issued in European Patent Application No. 08768441.1 and dated Jul. 22, 2010.

Examination Report issued in New Zealand Patent Application No. 581,710 and dated Oct. 29, 2010.

Extended European Search Report issued in European Patent Application No. 11179459.0 and dated Oct. 21, 2011.

Shah S A et al, "A Comparative Review of Topical Therapies for inflammatory Bowel Disease", Clinical Immunotherapeutics, ADIS International, Auckland, NZ, vol. 6, No. 2, Jan. 1, 1996, pp. 117-129, XP009152557, ISSN: 1172-7039.

Vernia P et al, "Topical Treatment of Refractor Distal Ulcerative Colitis with 5-ASA and Sodium Butyrate", Digestive Diseases and Sciences, vol. 40, No. 2, 1995, pp. 305-307, XP009152811, ISSN: 0163-2116.

\* cited by examiner

MATERIALS AND METHODS FOR TREATMENT AND DIAGNOSIS OF DISORDERS ASSOCIATED WITH OXIDATIVE STRESS

CROSS-REFERENCE TO RELATED APPLICATIONS

The present application claims the benefit of priority from U.S. Provisional Application Ser. No. 61/414,047, filed Nov. 16, 2010. The present application is also a continuation in part of U.S. application Ser. No. 12/664,237, filed Dec. 11, 2009, which claims the benefit of priority from U.S. Provisional Application Ser. Nos. 60/934,505, filed Jun. 13, 2007, and 61/063,745, filed Feb. 6, 2008, and which is a continuation-in-part of U.S. application Ser. No. 11/540,864, filed Sep. 28, 2006, now abandoned, which is a continuation-in-part of U.S. application Ser. No. 11/107,179, filed Apr. 15, 2005, now abandoned, which is a continuation-in-part of U.S. application Ser. No. 10/927,742, filed Aug. 27, 2004, now U.S. Pat. No. 7,312,243, which claims the benefit of U.S. Provisional Application Ser. No. 60/499,152, filed Aug. 29, 2003. The contents of each of the foregoing are hereby incorporated herein by reference, including any figures, tables, nucleic acid sequences, amino acid sequences, and drawings.

BACKGROUND OF THE INVENTION

Ulcerative colitis (UC) is an inflammatory bowel disease characterized by recurrent bouts of rectal bleeding and bloody diarrhea. The initial inflammatory reaction begins in the rectal mucosa in over 95% of cases and may extend in a contiguous fashion to involve the whole colon (Hendrickson, 2002).

Histologically, ulcerative colitis is manifest by mainly neutrophil infiltration into the colonic mucosal crypts of Lieberkuhn leading to a neutrophilic cryptitis and the formation of micro crypt abscesses, which coalesce to form bleeding macroscopic mucosal ulcerations. Neutrophilic secretion of tissue destructive cytokines and oxygen radicals leads to a chronic crypt destructive colitis that can involve the entire colon (Carpenter, 2000).

On a populational level, ethnic variation of glutathione peroxidase has been recorded with individuals of Jewish or Mediterranean origin exhibiting lower activities (*The Metabolic and Molecular Basis of Inherited Disease*, 2001, 8th ed., p. 4650). A two to four fold increase in incidence and prevalence of ulcerative colitis has also been reported for these ethnic groups (Roth et al., 1989).

There remains a need in the art for therapeutic modalities to treat inflammatory bowel diseases such as ulcerative colitis. The present invention addresses this need.

BRIEF SUMMARY OF THE INVENTION

Methods of treating ulcerative colitis in mammals in accordance with the present invention include orally administering alpha-lipoic acid daily; and rectally administering an enema including aminosalicylic acid; a steroid; a mast cell stabilizer; and a short chain fatty acid; to a mammal in need thereof. In some aspects of the invention, the enema is administered daily and the contents are retained for at least about 4 hours. In other aspects of the invention, the enema is administered daily for about six weeks and then about twice weekly thereafter.

Another aspect of the invention includes methods of decreasing an ulcerative colitis Mayo Score in a mammal in need of such treatment by: determining the ulcerative colitis Mayo Score of a mammal in need of treatment; administering to the mammal: orally alpha-lipoic acid daily; and rectally an enema including aminosalicylic acid; a steroid; a mast cell stabilizer; and a short chain fatty acid; wherein the enema is administered daily and the contents of which are retained for at least about 4 hours; and repeating the daily administering step until a decrease in the ulcerative colitis Mayo Score of ≥3 is observed.

The subject invention also concerns kits and containers comprising a therapeutic composition or compounds of the present invention. The containers can be selected for ease of administration of a therapeutic composition to a person or animal.

Unless defined otherwise, all technical and scientific terms used herein have the same meaning as is commonly understood by one of ordinary skill in the art to which this invention belongs. In the event that there is a plurality of definitions for a term herein, those in this will prevail unless stated otherwise.

As described herein, all the amounts disclosed herein are based on the weight of an average adult male, about 75 kg, and can be adjusted as needed using mg/kg.

DETAILED DISCLOSURE OF THE INVENTION

Figure 1A:
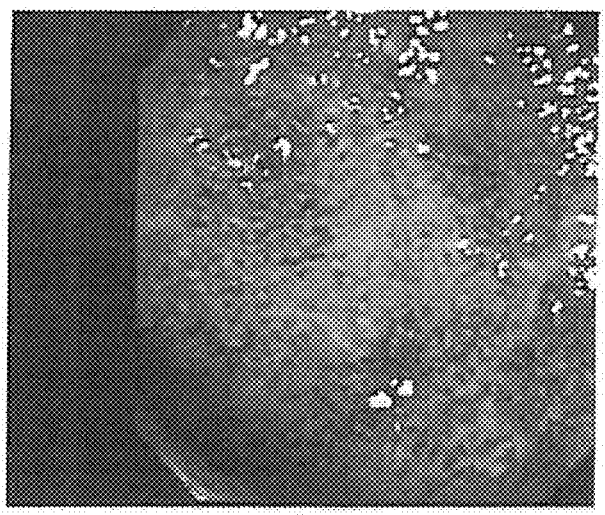
FIGS. 1A-1E show sigmoidoscopy results: distal sigmoid (FIG. 1A); distal sigmoid (FIG. 1B); mid-sigmoid (FIG. 1C); distal sigmoid (FIG. 1D); and rectum (FIG. 1E) corresponding to Example 3.
Figure 1B:
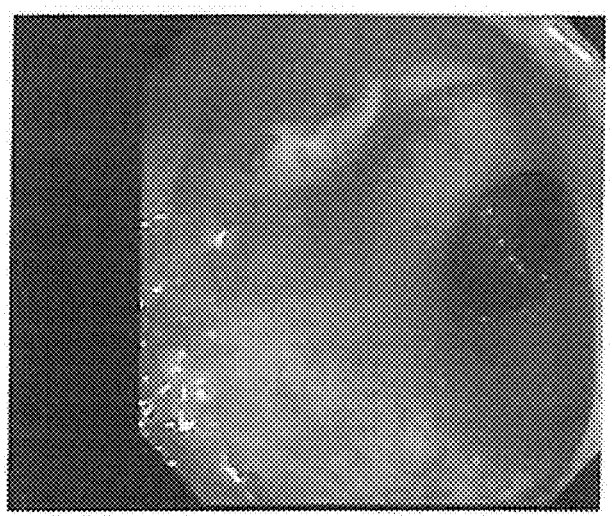
Figure 1C:
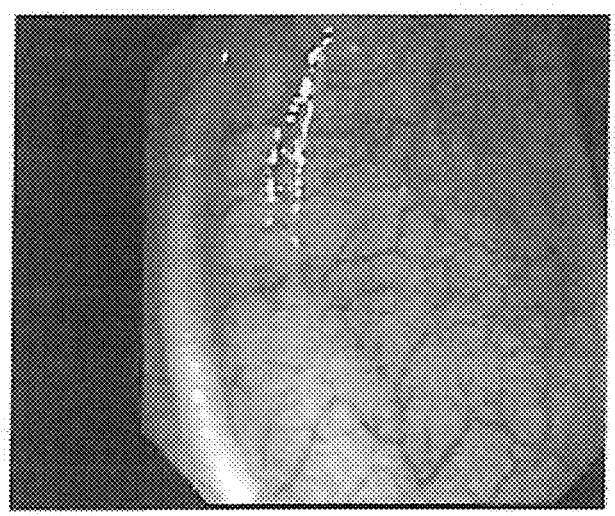
Figure 1D:
Figure 1E:
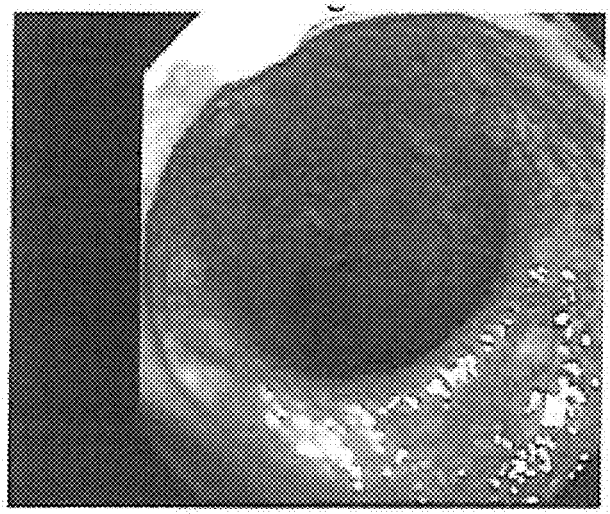

The subject invention concerns materials and methods for the prevention and treatment of disease conditions associated with oxidative stress or a compromised reducing environment.

One aspect of the invention concerns methods and compositions for treatment of inflammatory bowel disorders, such as Crohn's disease and ulcerative colitis, and irritable bowel disorder. The subject invention concerns methods for preventing and/or treating diseases that are caused or exacerbated by oxidative stress or that are caused by or exacerbated by a compromised intracellular or extracellular reducing environment. One embodiment of the subject invention concerns methods of preventing and/or treating a person or animal having an inflammatory bowel disorder, such as, for example, ulcerative colitis.

It has been discovered that the production of hydrogen peroxide ($H_2O_2$) and its overproduction and escape from cells of the gastrointestinal tract is a causal component of inflammatory bowel disorders such as ulcerative colitis. The cells of the body are constantly producing oxygen radicals, including hydrogen peroxide, as a by-product of metabolism. These radicals must be neutralized within the cells before they can damage intracellular structures and lead to cell death. The constant generation of oxygen radicals and hydrogen peroxide is an oxidative stress that is neutralized by the reducing capacity of the cell. The most important reducing substance within cell is glutathione. Thus, the reducing environment that cells require in order to function is maintained by a delicate balance between the reduction capacity of the cell (mainly glutathione) and oxygen radicals (mainly hydrogen peroxide). Under normal conditions the intracellular hydrogen peroxide concentration is maintained very low by the constant production of glutathione which neutralizes (reduces) $H_2O_2$. When this balance is disturbed either by increased $H_2O_2$ generation, decreased glutathione production or both, then hydrogen peroxide will accumulate within cells and diffuse through the cellular membrane to the extracellular space. When this occurs in the rectal tissues, the colonic barrier to luminal bacterial products is disrupted allowing tissue penetration of antigenic material into the normally sterile colonic lamina propria. The subsequent infiltration of activated neutrophils results in secretion of enormous amounts of tissue destructive cytokines and additional oxygen radicals including hydrogen peroxide. Thus, a vicious cycle is set up whereby cryptal neutrophils, upon exposure to fecal material, are stimulated to produce destructive cytokines and oxygen radicals in an attempt to rid the local environment of bacteria, which further damages the colonic tissue barrier thereby allowing additional bacterial infiltration with amplification of the immune response and so on until the entire colon is involved. The production of hydrogen peroxide by infiltrating neutrophils is able to diffuse into adjacent normal colonic tissue, overwhelming its reducing capacity and causing oxidative damage to adjacent colonic barrier function and epithelial cells. This results in a contiguous spread of inflammation from the point of origin in the rectum to the rest of the colon. Hydrogen peroxide that has diffused or escaped from a cell can be converted to a hydroxyl radical which can subsequently disrupt cellular structures such as the basement membrane and tight junctions. This initiates the immune response which results in the pathology associated with ulcerative colitis.

Ulcerative colitis can be divided into two phases. The first phase is called induction and begins with the extracellular diffusion of hydrogen peroxide to the extracellular environment. Throughout this phase the epithelial lining appears macroscopically intact and histologically normal. The damage is confined to molecular disruption of colonic epithelial tight junctions and basement membranes resulting in transitory increased colonic permeability to intestinal antigens. There is no rectal bleeding during this phase and this process may go on for months to years resulting in sporadic extra intestinal manifestations such as myalgias, arthralgias and faciitis due to intermittent immune activation subsequent to transitory colonic sub-mucosal antigenic penetration. Due to the high colonic epithelial turnover rate of about three days it is possible to repair the damage and restore the colonic barrier if the initial damage is not overwhelming. However, if the epithelial barrier cannot be reassembled and antigenic invasion is sustained, then further immune activation in the form of neutrophilic infiltration will occur.

The second phase of ulcerative colitis begins with neutrophilic invasion into the colonic tissues and is called the propagation phase. It is during this phase that neutrophil derived cytokines and oxygen radicals initiate tissue damage leading to mucosal ulceration and rectal bleeding and diarrhea characteristic of this disease.

The importance of two distinct phases of ulcerative colitis lies in the ability to modify the inflammatory process during the induction phase via manipulation of risk factors which can be positive (pro-inflammatory, increasing $H_2O_2$ production) or negative (anti-inflammatory, decreasing $H_2O_2$ production). The propagation phase, as the name implies, is self-sustaining and auto-stimulating, and is not affected by risk factors. It is during the propagation phase that individuals manifest rectal bleeding due to colonic tissue destruction and without external intervention to reverse the process may develop extensive colonic inflammation leading to colectomy. Colectomy will eliminate the source of induction and propagation along with that segment of intestine having a damaged and permeable barrier. This will abolish the portal of systemic antigenic entry and terminate the inflammatory process. However, colonic inflammation can be terminated anytime during induction if risk factors promoting $H_2O_2$ production are recognized and eliminated. Propagation can also be terminated by appropriate intervention to treat a patient with methods and compositions of the present invention.

Any materials that can be used to neutralize hydrogen peroxide or its decomposition products (hydroxyl radical or hydroxide anion) are contemplated within the scope of the invention. These include, but are not limited to, oxidizing agents, reducing agents, enzymes such as glutathione peroxidase and catalase, catalysts (such as zinc dust or other metal powders or metal catalysts), manganese in a bicarbonate buffer, and asbestos fibers or other fibers able to decompose hydrogen peroxide. Glutathione, or its precursor amino acids (glycine, cysteine and glutamate) can also be used in the compositions and methods of the invention. Monoester or diester glutathione derivatives can be used with the subject invention as glutathione with ester groups attached is taken up into cells more readily than glutathione.

In one embodiment, a therapeutic composition of the present invention comprises at least one reducing agent. The reducing agent can be one that acts primarily extracellularly, primarily intracellularly, or both extracellularly and intracellularly. In one embodiment, a therapeutic composition of the invention comprises at least one extracellular reducing agent and at least one intracellular reducing agent.

In an exemplified embodiment, the reducing agent is a thiosulfate ion, which can be provided in the form of a salt such as, for example, sodium thiosulfate, ammonium thiosulfate, calcium thiosulfate, potassium thiosulfate, silver thiosulfate, choline thiosulfate, gold sodium thiosulfate, magnesium thiosulfate hex hydrate, and thiosulfate hyposulfite. Examples of other reducing agents contemplated within the scope of the invention include, but are not limited to, metal borohydrides, sodium hydrosulfite, dimethylthiourea, sodium bisulfate, thiourea dioxide, diethylhydroxylamine, zinc dust, sodium cyanoborohydride, sodium hydride, trimethyl borate, benzyl triphenphosphonium chloride, butyl triphenphosphonium bromide, ethyl triphenphosphonium acid acetate, ethyl triphenphosphonium bromide, ethyl triphenphosphonium iodide, ethyl triphenphosphonium phosphate, and tetrabutyl phosphonium acid acetate. Another reducing agent that can be used is glutathione, or a monoester or diester glutathione, diester glutathione or multiester glutathione derivative.

In an exemplified embodiment, an intracellular reducing agent of the invention is alpha lipoic acid (ALA), dihydro lipoic acid, or pyruvate. Both of these are capable of entering a cell and reacting with $H_2O_2$. ALA is a small molecule (MW 206.3, CAS #1077-28-7). It is known by a variety of names which vary depending upon its redox state (oxidized or reduced) and the enantiomeric configuration around the number three carbon chiral center (*). The older relative (comparison) based D and L nomenclature has been replaced by the designation R and S indicating absolute stereochemical configuration.

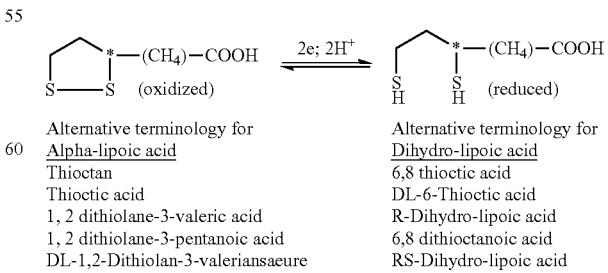

Alternative terminology for Alpha-lipoic acid
Thioctan
Thioctic acid
1, 2 dithiolane-3-valeric acid
1, 2 dithiolane-3-pentanoic acid
DL-1,2-Dithiolan-3-valeriansaeure Alternative terminology for Dihydro-lipoic acid
6,8 thioctic acid
DL-6-Thioctic acid
R-Dihydro-lipoic acid
6,8 dithioctanoic acid
RS-Dihydro-lipoic acid ALA is an eight carbon cyclic disulfide containing fatty acid which is synthesized in trace amounts within mitochondria in all cells of the body. Only the R-isomer is synthesized naturally. In its natural state ALA is covalently bonded, via its terminal carboxyl in an amide linkage, to the epsilon amino group of lysine residues which form part of multi-subunit enzyme complexes that catalyze vital energy metabolism reactions within mitochondria. There is very little free ALA in the cytoplasm or circulation.

The bonding of ALA to its cognate protein is accomplished as a post-translational modification of the enzyme. In its protein bound state it is a required enzymatic co-factor called lipoamide. The enzyme complexes which use ALA are the pyruvate dehydrogenase complex which catalyzes the conversion of pyruvate to acetyl-CoA, a vital substrate for energy production via the Krebs (citric acid) cycle. The alpha-ketoglutarate complex which catalyzes another important Krebs cycle reaction, the branched chain alpha-keto acid dehydrogenase complex which catalyzes the oxidative decarboxylation of three branched chain amino acids (valine, leucine and isoleucine) generating acetyl-CoA for entry into the Krebs cycle and finally the glycine cleavage system complex that catalyzes the formation of 5,10 methylene tetrahydrofolate which plays a vital role in the synthesis of nucleic acids.

The natural function of ALA is to bind and transfer acyl groups to successive enzymatic active sites among the subunits of each enzyme complex. In this process of acyl transfer ALA is reduced to dihydrolipoic acid and subsequently re-oxidized back to ALA by its attached cognate enzyme which readies it for the next acyl transfer. ALA has a high degree of bioavailability after oral administration and exhibits both lipid and water solubility. This allows its distribution to both intra and extra cellular compartments.

A therapeutic composition of the present invention can optionally include one or more of the following:

1) a compound or composition that is antibacterial or that prevents or inhibits adherence of bacteria to gastrointestinal tissues or cells. In one embodiment, the compound can be a bismuth salt. In an exemplified embodiment, the compound can be bismuth subgallate. Antibiotics active against bacteria present in the gastrointestinal tract can be included. In a preferred embodiment, the compound is active against Bacteroides.

2) a compound or composition that adds viscosity (for steric hindrance) and/or that inhibits epithelial lipid peroxidation, such as, for example, d-alpha-tocopherol (vitamin E), carboxymethylcellulose or other viscous mono or polysaccharide compounds (e.g., honey).

3) a compound or composition that inhibits mast cells and/or that helps to seal or repair tight junctions between cells in the gastrointestinal tract. In one embodiment, the compound can be sodium cromolyn.

4) a compound or composition that scavenges hydroxyl radicals. In one embodiment, the compound can be dimethyl sulfoxide (DMSO), mannitol, methional, deoxyribose or DMPO (5,5-dimethylpyrollidine-N-oxide).

5) a compound or composition that inhibits or blocks NADPH oxidase, such as DMSO or apocynin.

6) a compound or composition that kills or inhibits colonically localized neutrophils, or that prevents or inhibits neutrophils from entering the colon or exiting the colonic vasculature. In one embodiment, antibodies or other blocking agents of vascular adhesion molecules (ICAMS) present on vascular endothelium, such as selectin, or antibodies or other blocking agents of the corresponding neutrophilic counter ligand, such as integrin, can be used.

7) a compound or composition that stops or inhibits neutrophils from producing hydrogen peroxide. Examples include DMSO and Trental.

8) a compound or composition that chelates or sequesters iron molecules that are necessary for the reduction of hydrogen peroxide to a hydroxyl radical. In one embodiment, the iron chelating agent Desferal (Deferoxamine) can be used.

9) the compound 5-aminosalicylic acid (5-ASA) or colazal (balsalazide disodium) can be included.

10) a compound that neutralizes or scavenges hydroxide ions. In one embodiment, a composition of the invention can comprise a weak acid or weak base, such as in the form of a buffered solution at a pH of from about 6.8 to about 7.4 comprising sodium bicarbonate.

11) any agent or therapy that will inhibit the electron transport chain or any of its components (e.g., an agent or therapy that suppresses cytochrome oxidase enzyme).

In one embodiment, a composition of the invention comprises a reducing agent and an NADPH-oxidase inhibitor. Preferably, the reducing agent is a thiosulfate salt, such as sodium thiosulfate, and the NADPH-oxidase inhibitor is apocynin. In a preferred embodiment, the composition is provided in an orally administered capsule that delays dissolving until it is present in the colon.

The compounds of the invention can be administered as a single composition, or they can be administered individually at the same or different times and via the same or different route (e.g., oral, rectal, etc.) of administration. In one embodiment, a composition of the invention is provided in a mixture or solution suitable for rectal instillation and comprises sodium thiosulfate, bismuth subgallate, vitamin E, and sodium cromolyn. In one embodiment, a therapeutic composition of the invention comprises, in a suppository form, butyrate, and glutathione monoester, glutathione diethylester or other glutathione ester derivatives. The suppository can optionally include sodium thiosulfate and/or vitamin-E.

The subject invention also concerns methods for preventing and/or treating radiation induced proctitis that can result from radiation treatment of prostate cancer and other disease conditions. Other disease conditions that can be prevented and/or treated using methods and compositions of the present invention include, but are not limited to, Parkinson's disease, cataracts, cerebral palsy, and gastrointestinal cancers, such as stomach and colon cancers. Compositions of the present invention can also be used to treat or prevent pouchitis after a colectomy. Pouchitis is an inflammation of the "J" pouch that is surgically constructed from the last foot of small intestine after the colon is taken out. The last six inches of small intestine is bent up and sewn back onto the small intestine. The hole is made at the bend of the "J" and that is connected to the anus. The purpose is to have a reservoir for stool to avoid the external bag.

The small intestine is more permeable to luminal contents and having stool stored in it in that fashion can lead to inflammation due to the increased bacterial load and increased oxidative stress. Compositions formulated for administration as an enema or oral administration can be used to treat or prevent pouchitis.

The subject invention also concerns methods for treating hemorrhoids. In one embodiment, a liquid enema formulation of the invention is applied directly to the hemorrhoid. In a specific embodiment, a liquid enema formulation of the invention is placed on a suitable material such as gauze or an absorbent pad and the enema containing material is contacted with the hemorrhoid, typically for about 2 to 4 hours. This application is typically performed once or twice daily.

In one embodiment of the subject methods, a person or animal in need of treatment is administered an effective amount of a therapeutic composition of the present invention in a biologically compatible form or composition. For preventative therapy, an effective amount of a therapeutic composition of the invention is administered to a person or animal prior to onset of the condition to be treated. For example, an effective amount of a therapeutic composition of the invention is administered prior to radiation treatment of prostate cancer in order to prevent radiation induced proctitis. In an exemplified embodiment, the reducing agent of the composition is ALA and/or dihydro lipoic acid and/or pyruvate and/or 5-ASA and/or a thiosulfate salt such as, for example, sodium thiosulfate. In one embodiment, the therapeutic composition is administered rectally or by delayed dissolving oral capsule. Delayed dissolution dosage forms include pH-dependent capsules and coatings that only dissolve at the pH associated with the colonic environment. Examples of pH-dependent materials include, but are not limited to, methyl methacrylate, methacrylic acid and/or ethyl acrylate polymers, including for example, ammonio methacrylate copolymer. Other dosage forms for delivery of a composition of the invention to the colon include, for example, time-dependent delivery systems, pressure-dependent delivery systems, bacterial-dependent systems (Basit et al., 2003). Also contemplated are dosage forms that utilize oxidation potential-dependent systems. Colon content has a much higher oxidative potential than the small intestinal contents since many times more bacteria are present in the colon. An oxidation potential-dependent system is a delivery system that is sensitive to oxidation potential and releases its contents or becomes active when the capsule is exposed to the higher oxidation level in the colon. This can be in the form of a prodrug which is degraded to the active drug when oxidized and capsules which dissolve when exposed to the high level of oxidation in the colon. In one embodiment, a combination of rectally and orally administered compositions are given to a patient, particularly if the patient has rectal bleeding. After bleeding is controlled, rectal therapy can optionally be discontinued and oral therapy maintained as necessary. Thiosulfates, such as sodium thiosulfate can optionally be administered in a solution intravenously, e.g., solutions of from about 10% to about 25% (w/v) sodium thiosulfate can be given. Methods of the present invention also contemplate institution of lifestyle changes of the patient, as described herein, either alone or in conjunction with the use of therapeutic compositions of the invention.

Dosage ranges for the various compounds to be administered to an individual patient can be determined by an ordinarily skilled clinician. Examples of dosage ranges provided herein are for guidance and should not be construed as limiting the scope of the invention in regard to dosages that can be administered. Dosage ranges can be, for example:

sodium thiosulfate: 150-250 mg/kg body weight
alpha lipoic acid 10-20 mg/kg body weight
dihydro lipoic acid 10-20 mg/kg body weight
pyruvate 50-100 mg/kg body weight
bismuth subgallate: 2-4 mg/kg body weight
vitamin E: 25-30 IU/kg body weight
cromolyn sodium: 1-3 mg/kg body weight In one embodiment, the components sodium thiosulfate, bismuth subgallate, vitamin E, and cromolyn sodium can be prepared in a retention enema in sterile water according to the following:

Step 1: Dissolve sodium thiosulfate in water by gently shaking until all crystals are dissolved.
Step 2: Add cromolyn sodium until completely dissolved.
Step 3: Add bismuth subgallate and gently shake until completely suspended.
Step 4: Add vitamin E and shake until suspended.

The methods of the present invention also include oral administration of a drug that lowers endogenous catecholamines, such as clonidine, where such treatment is indicated by the symptoms and risk factors presented by the patient. Monoamine oxidase (MAO) inhibitors that inhibit or prevent mitochondrial MAO from metabolizing endogenous catecholamines can also be administered as part of a patient treatment regimen and is contemplated within the scope of the present invention. Preferably, the MAO inhibitor is one that does not pass through the blood-brain barrier. In one embodiment of the invention, a combination of clonidine (or a similar drug) and an MAO inhibitor is administered to a patient.

Also contemplated within the scope of the invention is the administration of NADPH-oxidase inhibitors, such as Trental (pentoxifylline) and apocynin; these can be administered as a delayed dissolving oral capsule that dissolves in the colon, or as a rectal solution. Pentoxifylline has anti-inflammatory activity and may function as a purinergic agonist via an adenosine receptor on the surface of the infiltrating neutrophil which can inhibit NADPH oxidase and apoptosis. This oral therapy can be continued, along with lifestyle changes, as maintenance therapy to prevent re-induction and relapse.

In one embodiment, a composition of the invention comprises a reducing agent and an NADPH-oxidase inhibitor. In one embodiment, the reducing agent is a thiosulfate salt, such as sodium thiosulfate, and/or 5-ASA and/or ALA and/or dihydro lipoic acid and/or pyruvate, and the NADPH-oxidase inhibitor is apocynin. In one embodiment, the composition is provided in an orally administered form, such as a capsule, that dissolves in a subject's stomach and/or small intestine. In another embodiment, the composition is provided in an orally administered capsule that delays dissolving until it is present in the colon. Delayed dissolution dosage forms include pH-dependent capsules and coatings that only dissolve at the pH associated with the colonic environment. Examples of pH-dependent materials include, but are not limited to, methyl methacrylate, methacrylic acid and/or ethyl acrylate polymers, including for example, ammonio methacrylate copolymer. Other dosage forms for delivery of a composition of the invention to the colon include, for example, time-dependent delivery systems, pressure-dependent delivery systems, bacterial-dependent systems (Basit et al., 2003). Also contemplated are dosage forms that utilize oxidation potential-dependent systems.

Another aspect of the subject invention concerns compositions formulated for administration as an enema. An enema formulation of the invention comprises a reducing agent (or any other agent having a similar mode of action) and a steroid. In one embodiment, an enema formulation of the invention comprises an aminosalicylic acid, such as 5-ASA (5-aminosalicylic acid; also known as mesalamine), or 4-ASA (4-aminosalicylic acid), or any analog or derivative of a salicylic acid, and a steroid compound. In another embodiment, the composition comprises sulfasalazine (Azulfidine) as the reducing agent. Steroid compounds contemplated within the scope of the invention include corticosteroids. In an exemplified embodiment, the steroid comprises budesonide, or an analog or derivative thereof. In a specific embodiment, a composition suitable for administration as an enema comprises an effective amount of 5-ASA and budesonide. In another specific embodiment, a composition of the invention comprises 5-ASA and a hydrocortisone compound, such as CORTENEMA. Other corticosteroids that can be used in the present invention include, but are not limited to, prednisone, prednisolone, betamethasone, beclometasone, and tixocortol. The enema formulation can optionally comprise polysorbate-80 (or any other suitable emulsifying agent), and/or any short chain fatty acid (e.g., a five, four, three, or two carbon fatty acid) as a colonic epithelial energy source, such as sodium butyrate (4 carbons), proprionate (3 carbons), acetate (2 carbons), etc., and/or any mast cell stabilizer, such as cromolyn sodium (GASTROCROM) or Nedocromil sodium (ALOCRIL). In a further embodiment, an enema formulation of the invention can comprise ALA. In one embodiment, the ALA is provided as a racemic mixture of the R and L isomers of ALA. In another embodiment, the ALA is provided as R-alpha-lipoic acid. In another embodiment, the ALA is provided as R-dihydro lipoic acid. In one embodiment, an enema formulation of the invention comprises an effective amount of 5-ASA, budesonide, sodium butyrate, cromolyn sodium, and optionally an alpha-lipoic acid, such as R-dihydro lipoic acid.

As used herein, ulcerative colitis Mayo scores were calculated using the following scale:

| Assessment | Finding |
|---|---|
| Stool Frequency | 0 = Normal number of stools |
| | 1 = 1-2 more stools per day than normal |
| | 2 = 3-4 more stools per day than normal |
| | 3 = ≥5 more stools per day than normal |
| Rectal Bleeding | 0 = No blood seen |
| | 1 = Streaks of blood with stool less than half the time |
| | 2 = Obvious blood with stool most of the time |
| | 3 = Blood alone passes |
| Endoscopic Findings | 0 = Normal or inactive disease |
| | 1 = Mild disease (erythema, decreased vascular pattern, mild friability, erosions) |
| | 2 = Moderate disease (marked erythema, lack of vascular pattern, friability, erosions) |
| | 3 = Severe disease (spontaneous bleeding, ulceration) |
| Physician's Global Assessment | 0 = Normal |
| | 1 = Mild disease |
| | 2 = Moderate disease |
| | 3 = Severe disease |

The ulcerative colitis Mayo Scoring System ranges from 0 to 12 points. The physician adds the scores from each of the four components of the scoring system for a total score. A higher number of total points indicates more severe disease, as specified below:

0-4 points=Mild, normal or inactive disease;
5-8 points=Moderate disease (marked erythema, lack of vascular pattern, friability, erosions);
9-12 points=Severe disease (spontaneous bleeding, ulceration).

Each patient is responsible for determining the degree of abnormality of his or her stool frequency. The daily bleeding score represents the most severe bleeding of the day. The Physician's Global Assessment is the physician's assessment of the severity of disease, based on acknowledgement of the three other components used in the ulcerative colitis Mayo Score (stool frequency, rectal bleeding, and endoscopic findings), as well as the patient's report of daily abdominal discomfort and sense of well being, and other observations (e.g., physical findings, patient's Performance Status).

Histology is scored with the following scale:

| Score | Degree Of Activity | Description/Definition |
|---|---|---|
| 0 | Quiescent or Minimal | Absence of neutrophilic cryptitis or very rare neutrophils in crypt epithelium with a normal complement of mononuclear cells in the lamina propria or borderline plasma cell excess in the lamina propria |
| 1 | Mild | Modest plasma cell excess in the lamina propria, usually patchy but can be diffuse, with multifocal neutrophilic cryptitis; rare crypt abscess formation is acceptable |
| 2 | Mild to Moderate | More diffuse plasma cell excess in the lamina propria, can be focal but typically diffuse, with multifocal neutrophilic cryptitis and crypt abscess formation |
| 3 | Moderate | Dense diffuse plasma cell excess in the lamina propria with multifocal crypt abscess formation |
| 4 | Moderate to Severe | Moderate with foci of surface epithelial sloughing/mucosal erosion |
| 5 | Severe | Extensive mucosal ulceration with a plasma cell rich ulcer base; viable mucosa shows diffuse crypt abscess formation |

For purposes of the present invention, a clinical response to treatment of ulcerative colitis shall be understood to include a decrease in an ulcerative colitis Mayo Score of preferably greater than or equal to about 3 points. Clinical remission shall be understood to include an ulcerative colitis Mayo Score of less than or equal to about 2. As used herein, histological remission shall be understood to be an ulcerative colitis Histology Score of about zero. Complete histological remission shall be understood to include an ulcerative colitis Mayo Score of less than or equal to about 2, an ulcerative colitis Mayo Endoscopy Subscale Score of less than or equal to about 1 and an ulcerative colitis Histology Score of about zero. Preferably, the methods for treating ulcerative colitis with the compositions disclosed herein result in a positive clinical response after about six weeks of treatment. In some aspects, the inventive methods for treating ulcerative colitis result in a positive clinical response after about three weeks of treatment.

Another embodiment includes methods of treating ulcerative colitis in a mammal requiring such treatment. Such methods include administering to the mammal: orally from about 100 mg to about 1000 mg of alpha lipoic acid or pharmaceutically acceptable salt thereof; and rectally an enema including from about 500 mg to about 5000 mg of an aminosalicylic acid, from about 0.5 mg to about 10 mg of a steroid, from about 10 to about 1000 mg of a mast cell stabilizer, and from about 5 millimoles to about 50 millimoles (about 5 ml to about 50 ml of a 1 molar solution) of a short chain fatty acid; and allowing the contents of the enema to be retained for at least about 4 hours.

In one embodiment, the enema is prepared as follows:

Step 1: 5-ASA (ROWASA) is available in an enema bottle containing 4.0 grams in a 60 mL aqueous suspension. 20 mL of the 5-ASA solution is removed and discarded from the Mesalamine Rectal Suspension Enema (5-ASA).

Step 2: Budesonide is prepared by dissolving budesonide in water to a concentration of 5 mg/ml. 1 ml of the 5 mg/mL budesonide solution is then added to the remaining 40 mL of the 5-ASA in the enema bottle in Step 1 and mixed.

Step 3: Sodium cromolyn is available in a 5 mL ampule containing 100 mg of cromolyn sodium, USP, in purified water. 5 mL of the sodium cromolyn solution is added to the resulting solution in Step 2 and mixed.

Step 4: Sodium butyrate is prepared as a 1-N solution in water in accordance with standard preparation guidelines. 15 mL of the sodium butyrate solution is added to the resulting solution in Step 3 and mixed.

Preferably, the 4-component enema is dispensed in enema bottles, protected from light, and refrigerated. The enema is stable for storage in these conditions for about 30 days.

In some aspects, the alpha-lipoic acid is selected from racemic alpha-lipoic acid, R-lipoic acid, R-dihydro-lipoic acid and pharmaceutically acceptable salts thereof. Preferably, the alpha-lipoic acid is R-dihydro-lipoic acid. In other aspects, the aminosalicylic acid is selected from 5-ASA (mesalamine), 4-ASA, and analogs or derivatives thereof. Preferably, the aminosalicylic acid is 5-ASA. Suitable steroids include budesonide, hydrocortisone, prednisone, prednisolone, betamethasone, beclometasone, tixocortol, and analogs or derivatives thereof. Preferably, the steroid is budesonide. The mast cell stabilizer is cromolyn sodium or nedocromil sodium. Preferably, the mast cell stabilizer is cromolyn sodium. In some aspects, the short chain fatty acid is sodium butyrate, proprionate, or acetate. Preferably, the short chain fatty acid is sodium butyrate.

In one embodiment, the composition includes from about 100 mg to about 1000 mg of alpha-lipoic acid or pharmaceutically acceptable salt thereof, or from about 150 mg to about 750 mg of alpha-lipoic acid or pharmaceutically acceptable salt thereof, or from about 250 mg to about 600 mg of alpha-lipoic acid or pharmaceutically acceptable salt thereof. Preferably, the amount of alpha-lipoic acid or pharmaceutically acceptable salt thereof is from about 300 mg to about 600 mg. In a specific embodiment, about 300 mg of alpha-lipoic acid alpha-lipoic acid or pharmaceutically acceptable salt thereof is administered twice daily.

In another embodiment, the composition comprises from about 200 mg to about 5000 mg, or from about 500 mg to about 3,000 mg of 5-ASA, or from about 750 mg to about 1,500 mg of 5-ASA, or from about 1,250 mg to about 1,150 mg of 5-ASA. In another embodiment, the composition comprises about 2,600 mg of 5-ASA. In one embodiment, 5-ASA is applied at 30-40 mg/kg body weight. The composition can also comprise from about 0.5 mg to about 10 mg of budesonide or hydrocortisone or about 8 mg of hydrocortisone, or from about 1 mg to about 7.5 mg of budesonide or hydrocortisone or about 8 mg of hydrocortisone, or from about 2.5 mg to about 5 mg of budesonide. In a specific embodiment, the composition comprises about 0.5 mg or about 5 mg of budesonide. In one embodiment, budesonide is applied at 0.05-0.15 mg/kg body weight. If the composition comprises cromolyn sodium it can be present in an amount from about 10 mg to about 1000 mg, or from about 20 mg to about 200 mg, or from about 30 mg to about 100 mg. In a specific embodiment, cromolyn sodium is provided in an amount of about 70 mg. In another embodiment, the cromolyn sodium is provided in an amount of about 100 mg. If the composition comprises polysorbate-80, it can be provided at a concentration from about 1% (v/v) to about 10% (v/v). If the composition comprises sodium butyrate it can be present in an amount of from about 5 millimoles to about 50 millimoles, i.e. about 5 ml to about 50 ml of a 1 molar solution. Preferably, the amount of sodium butyrate is about 15 millimoles, i.e. about 15 ml of a 1 molar solution. Alternatively, sodium butyrate can be present in an amount of from about 500 to about 1500 mg. In one embodiment, sodium butyrate is applied at 4-6 mM/kg body weight. In a specific embodiment, polysorbate-80 is provided in the composition at a concentration of about 6% (v/v).

In some aspects, the volume of the enema administered is from about 40 ml to about 80 ml. Preferably, the volume of the enema administered is about 60 ml.

In an exemplified embodiment, a composition suitable for administration as an enema is formulated as follows: 17 cc of 5-ASA (about 1,150 mg of 5-ASA), 1 cc of budesonide (at 5 mg per cc), 2 cc of cromolyn sodium (at 20 mg per cc), and polysorbate-80 at 6% (v/v). In another specific embodiment, a composition comprises 10 cc of hydrocortisone (16.6 mg total), 30 cc of 5-ASA (2 gm total), and optionally alpha-lipoic acid and/or L-glutamine and/or N-acetyl cysteine and/or 5 cc cromolyn sodium (100 mg), and/or 12.5 cc sodium butyrate (1.1 gm).

In a specific embodiment, an enema formulation of the invention comprises 5-ASA, budesonide, cromolyn sodium, and sodium butyrate. A formulation for oral administration includes R-dihydrolipoic acid. The enema formulation can comprise, for example, about 0.5 to 5 grams of 5-ASA; about 0.5 to 10 mg of budesonide; about 10 to 1000 mg of cromolyn sodium; and about 5 to 50 millimoles of sodium butyrate. The formulation for oral administration can include, for example, at least about 600 mg of R-alpha-lipoic acid or R-dihydrolipoic acid. In a more specific formulation, the enema can be prepared to comprise about 2.7 grams of 5-ASA (40 cc of a 60 cc bottle of 5-ASA containing 4 grams of 5-ASA in the 60 cc); about 5 mg budesonide (in 1 cc); about 100 mg cromolyn sodium (in 5 cc); and about 15 millimoles of sodium butyrate (15 cc of a 1 molar solution of sodium butyrate in water).

Enema compositions of the invention can be administered to a patient on dosage and schedule as determined by a clinician. In one embodiment, an enema of the invention can be administered daily. Preferably, the enema is retained for at least about 5 hours. More preferably, the enema is retained between about 6 hours to about 12 hours. In some embodiments the enema is administered daily at night, preferably at bedtime. Optionally, the enema can be alternated every other day with an enema that contains the reducing agent, e.g. 5-ASA, and optionally the cromolyn sodium and/or polysorbate-80 but without the steroid. In one embodiment, a patient is given an enema of the invention daily for approximately a month. Optionally, in the second month of treatment, the amount of steroid in the enema is reduced over time; for example, the steroid can be reduced over four weeks of treatment until no steroid is administered in the enema (e.g., at the start of the third month of treatment). In some aspects, the enema is administered daily for about six weeks, and twice weekly thereafter. In the third month of treatment, an enema of the invention to be administered daily to a patient may comprise the reducing agent (e.g., 5-ASA), and a short chain fatty acid (e.g., sodium butyrate) but omitting the steroid. In a fourth month of treatment, an enema of the invention to be administered daily to the patient may comprise the reducing agent but omit the short chain fatty acid and the steroid. In a fifth month of treatment, a patient may receive the same enema as in the fourth month but every other day or, optionally, on an as needed basis.

The subject invention also concerns compositions formulated for oral administration. These oral compositions can be administered as a separate treatment or in conjunction with enema formulations of the invention. In some aspects, the oral component is administered at least once daily. In other aspects the oral component is administered twice daily. In one embodiment, compositions of the invention are administered orally during enema treatment, and continue after cessation of enema treatment. In one embodiment, a composition comprises an oral reducing agent such as an alpha-lipoic acid or any oral agent which directly, or indirectly through an intermediary mechanism, acts as an intracellular or extracellular reducing agent and neutralizes or otherwise prevents the formation of intra or extracellular hydrogen peroxide or oxygen radicals. Other oral reducing agents contemplated within the scope of the invention include, but are not limited to, sodium thiosulfate, mercaptopropionylglycine, N-acetylcysteine, glutathione, melatonin, CoQ 10, Ebselen, and an aminosalicylic acid such as 5-aminosalicylic acid (5-ASA). 5-ASA is also available as an oral formulation (in addition to an enema formulation) (including, for example, Azulfidine, Asacol, Dipentum, mesalamine, Balsalazide, Olsalazine) and is capable of neutralizing extracellular peroxide and oxygen radicals. The alpha-lipoic acid can be racemic alpha-lipoic acid, R-lipoic acid, R-dihydro-lipoic acid, S-lipoic acid, and/or S-dihydro-lipoic acid. In one embodiment, the alpha-lipoic acid is administered at 5-10 mg/kg. In a specific embodiment, about 100 mg to 1000 mg or more of alpha-lipoic acid, preferably as the R-dihydro-lipoic acid, is orally administered daily to a patient. In a more specific embodiment, about 600 mg of alpha-lipoic acid, preferably as the R-dihydro-lipoic acid, is orally administered daily to a patient; optionally, the patient can receive about 300 mg of the alpha-lipoic acid, preferably as the R-dihydro-lipoic acid, twice daily.

Another embodiment includes methods of decreasing the ulcerative colitis Mayo Score in a mammal in need of such treatment. The methods include administering to the mammal: orally from about 100 mg to about 1000 mg of alpha-lipoic acid or a pharmaceutically acceptable salt thereof; and rectally an enema including from about 500 mg to about 5000 mg of an aminosalicylic acid, from about 0.5 mg to about 10 mg of a steroid, from about 10 mg to about 1000 mg of a mast cell stabilizer, and from about 5 millimoles to about 50 millimoles (about 5 ml to about 50 ml of a 1 molar solution) of a short chain fatty acid; allowing the contents of the enema to be retained for at least about 4 hours, and repeating said daily administration until a decrease in the ulcerative colitis Mayo Score of greater than or equal to about 3 is observed.

Preferably, the methods for treating ulcerative colitis with the compositions disclosed herein result in a clinical response after about six weeks, or more preferably after about three weeks, of treatment. Preferably, the methods for treating ulcerative colitis with the compositions disclosed herein result in clinical remission after about six weeks, or more preferably after about three weeks, of treatment. Preferably, the methods for treating ulcerative colitis with the compositions disclosed herein result in histological remission after about six weeks, or more preferably after about three weeks, of treatment. Preferably, the methods for treating ulcerative colitis with the compositions disclosed herein result in complete histological remission after about six weeks, or more preferably after about three weeks, of treatment.

In one embodiment, an oral composition of the invention comprises alpha-lipoic acid, and/or N-acetyl-L-cysteine (N-A-C), and/or L-glutamine. A composition of the present invention can also comprise compounds that inhibit tissue necrosis factor (TNF). TNF inhibitory compounds contemplated within the scope of the invention include resveratrol, stinging nettle leaf extract, and berberine. A composition of the present invention can also optionally include compounds that directly neutralize $H_2O_2$ (e.g., calcium pyruvate), compounds that help protect the proteins from oxidation and degradation (e.g., L-carnosine), and/or compounds that are protective of nucleic acids (e.g., calcium D-glucarate). The composition can also optionally comprise one or more of the following: selenium, vitamin B-2 (riboflavin), vitamin B-12, folic acid, and biotin. In a specific embodiment, a composition of the invention comprises 300 mg of R-dihydro-lipoic acid, 500 mg N-A-C, 500 mg L-glutamine, 200 µg selenium, 100 mg vitamin B-2, 500 µg vitamin B-12, 800 µg folic acid, 2,000 µg biotin, 1,500 mg calcium pyruvate, 150 mg resveratrol, 275 mg stinging nettle leaf extract, and 200 mg raw stinging nettle leaf powder, berberine in the form of golden seal root complex 150 mg and golden seal powder 300 mg, 1,000 mg L-carnosine, and 250 mg calcium D-glucarate.

In one embodiment, the composition is provided in an orally administered form, such as a capsule, that dissolves in a subject's stomach and/or small intestine. In another embodiment, the composition is provided in an orally administered capsule that delays dissolving until it is present in the colon. Delayed dissolution dosage forms include pH-dependent capsules and coatings that only dissolve at the pH associated with the colonic environment. Examples of pH-dependent materials include, but are not limited to, methyl methacrylate, methacrylic acid and/or ethyl acrylate polymers, including for example, ammonio methacrylate copolymer. Other dosage forms for delivery of a composition of the invention to the colon include, for example, time-dependent delivery systems, pressure-dependent delivery systems, bacterial-dependent systems (Basit et al., 2003). Also contemplated are dosage forms that utilize oxidation potential-dependent systems.

The enema compositions and the oral compositions of the invention can be administered in conjunction with changes in a patient's diet. Dietary changes contemplated within the scope of the present invention include increased consumption of mineral oil, insoluble fiber, soluble fiber, prune juice, and VSL#3. It is preferable that alcohol be avoided in the diet of the patient being treated.

The methods and compositions of the present invention can be used with humans and other animals. Compositions of the present invention can be administered to an animal in need of treatment as described herein, i.e., orally, and/or as an enema, etc. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

As noted above, the oral and enema compositions of the invention can be administered independently or in conjunction together to a person or animal in need of treatment. Thus, in one embodiment, a method of the invention comprises administering an effective amount of only an oral composition of the invention, or an effective amount of only an enema composition of the invention, or an effective amount of both an oral and an enema composition of the invention to a person or animal in need of treatment. In one embodiment, an effective amount of an oral composition comprising an ALA (such as R-dihydro-lipoic acid) and an effective amount of an enema composition comprising an aminosalicylic acid (such as 5-ASA), and/or any suitable steroid (such as budesonide), and/or any mast cell stabilizer (such as cromolyn sodium), and/or any short chain fatty acid (such as sodium butyrate), and optionally an emulsifying agent (such as polysorbate-80), are administered to the person or animal. The oral and enema compositions can be administered daily, or every other day or every other two days, or every other three days, etc., or weekly, or on any other schedule as determined to be appropriate by the ordinarily skilled artisan. The oral and enema compositions can be administered on alternate days, e.g., oral on day one, enema on day two, etc. In one embodiment, the oral composition is administered every day, and the enema composition is administered every other day, or every two days, or every three days, or every four days, or every five days, or every six days, or once a week, etc. The oral and enema compositions can also be administered independently one or more times (e.g., two times, three times, etc.) per day.

Compounds useful in the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with compounds include ethanol, dimethyl sulfoxide, glycerol, alumina, starch, and equivalent carriers and diluents. To provide for the administration of such dosages for the desired therapeutic treatment, new pharmaceutical compositions of the invention will advantageously comprise between about 0.1% and 45%, and especially, about 1 and 15% by weight of the total of one or more of the compounds based on the weight of the total composition including carrier or diluent.

The subject invention also concerns dosage forms of the compounds and compositions of the invention. In one embodiment, compounds and compositions are provided in orally or rectally administered dosage forms. °A dosage form for oral administration comprising a capsule that dissolves in the colon and containing an effective amount of i) a reducing agent, for example, 5-ASA and/or sodium thiosulfate and/or APA and/or dihydro lipoic acid and/or pyruvate and/or an alpha-lipoic acid, and optionally ii) an NADPH-oxidase inhibitor, for example, apocynin, is specifically contemplated in the present invention. Delayed dissolution dosage forms include pH-dependent capsules and coatings that only dissolve at the pH associated with the colonic environment. Examples of pH-dependent materials include, but are not limited to, methyl methacrylate, methacrylic acid and/or ethyl acrylate polymers, including for example, ammonio methacrylate copolymer. Other dosage forms for delivery of a composition of the invention to the colon include, for example, time-dependent delivery systems, pressure-dependent delivery systems, bacterial-dependent systems (Basit et al., 2003). Also contemplated are dosage forms that utilize oxidation potential-dependent systems.

The compounds of the subject invention can also be administered utilizing liposome technology, slow release capsules, implantable pumps, biodegradable containers and other means known in the art. These delivery vehicles and methods can, advantageously, provide a uniform dosage over an extended period of time.

The subject invention also concerns containers comprising a therapeutic composition of the present invention. The containers can be selected for ease of storage and/or administration of a composition to a person or animal, e.g., a container can be one suitable for use in rectal administration of a therapeutic composition. The containers can be composed of any suitable material, including glass, plastic, etc. and can be disposable and/or recyclable. Therapeutic compositions of the present invention are preferably provided as a sterile composition in a sterile container. The subject invention also concerns kits comprising, in one or more containers, a therapeutic composition or compound of the invention. In one embodiment, a kit of the invention comprises, in one or more containers, a reducing agent, and/or an aminosalicylic acid, and/or a steroid, and/or a short chain fatty acid, and/or an emulsifying agent, and/or an antibacterial and/or antiadherence agent, and/or a viscosity enhancing and/or lipid peroxidation inhibitor, and/or a mast cell inhibitor and/or a mast cell stabilizer, and/or an agent that repairs, seals, or regenerates tight junctions between cells, e.g., an epidermal growth factor (EGF). In an exemplified embodiment, the kit comprises the compounds sodium thiosulfate, bismuth subgallate, vitamin E, and sodium cromolyn. In another embodiment, a kit comprises 5-ASA, budesonide, cromolyn sodium, and sodium butyrate. The compounds of the invention can be provided in a kit in a single pre-mixed dosage form, or in individual dosage units that are mixed together prior to administration, or that are administered individually. In one embodiment, a kit of the invention comprises compounds of an enema formulation of the invention and materials or articles for effecting administration of an enema.

All patents, patent applications, provisional applications, and publications referred to or cited herein are incorporated by reference in their entirety, including all figures and tables, to the extent they are not inconsistent with the explicit teachings of this specification.

EXAMPLES

Following are examples which illustrate procedures for practicing the invention. These examples should not be construed as limiting. All percentages are by weight and all solvent mixture proportions are by volume unless otherwise noted.

Example 1

Treatment of Patient During Induction Phase

It has been discovered that ulcerative colitis, like many other diseases can be mitigated if it is recognized during the induction phase. Recognition of the induction process is difficult since there are little or no symptoms or signs pointing to the colon as the source of the problem and the colon is histologically and macroscopically normal. Recognition at this stage requires a high index of suspicion coupled with some knowledge of the extra intestinal Manifestations, xenobiotic associations, family and genetic history, ulcerative colitis epidemiological data and life style history.

A p-anca antibody at this time may be positive if the colonic epithelial barrier has been rendered sufficiently permeable to allow prolonged contact between the immune system and bacterial antigens in the colon. The p-anca antibody has been shown to be directed against a surface antigen of *B. Vulgatus* and is an indication of colonic barrier breach with subsequent immune activation. Evidence of increased colonic epithelial turnover may be found in fecal samples since $H_2O_2$ can induce epithelial proliferation. If a colonoscopy should be performed additional evidence of epithelial cell proliferation may be seen such as melanosis coli (Pardi et. al., 1998). Immunological staining of colonic biopsies may reveal altered tight junction proteins such as cadherin and basement membrane abnormalities. In viva conductance studies, if this were possible, would show increased permeability in macroscopically normal colonic tissue.

In patients that are determined to be in the induction phase, measures can be undertaken to implement lifestyle changes in order to reduce the oxidative stress on the colon. All xenobiotics and alcohol should be terminated. Smoking should be discontinued gradually rather than via a complete cessation, i.e., the patient should avoid going "cold turkey" when trying to stop smoking. Constipation should be corrected. Fast food should be eliminated and a diet high in antioxidants (vegetables and fruit), fiber, and good quality protein should be instituted. Stress reduction should be instituted with counseling if necessary.

Example 2

Treatment of Patient During Propagation Phase

Currently, individuals are almost never recognized during the induction phase and only seek medical help because of rectal bleeding when the propagation phase has already developed. A colonic neutrophilic inflammatory reaction into the colonic mucosa cannot be reversed with the same measures used during the induction phase, although it is prudent to institute them in order to prevent re-induction after reversal of the inflammatory reaction has been accomplished.

Treatment of colonic inflammation during the propagation phase comprises one or more of the following:
1. Neutralization of colonic hydrogen peroxide.
2. Reduction of neutrophilic stimulation by colonic bacteria.
3. Termination of colonic epithelial cell lipid peroxidation.
4. Reduction of colonic mucosal permeability.

Neutralization of hydrogen peroxide is critical in order to terminate continued tissue damage. This can be accomplished, for example, with rectal instillation of sodium thiosulfate that will neutralize hydrogen peroxide to water and non-reactive sulfate products.

The stimulatory effect of colonic bacteria, mainly anaerobic Bacteroides, on neutrophils can be mitigated with bismuth subgallate which prevents bacterial adherence to the colonic epithelium and is bactericidal.

Termination of colonic epithelial lipid peroxidation can be achieved with d-alpha tocopherol (vitamin E) as the acetate or the succinate. This also adds viscosity to the solution which creates a steric hindrance to prevent cytokines and radicals from interacting with their target tissue.

Finally, cromolyn sodium can block colonic mast cells and decrease colonic permeability to luminal antigens.

This therapy can be administered as a retention enema once daily.

Oral therapy with Clonidine to reduce the oxidative effects of endogenous catecholamines secondary to stress can also be instituted. Pentoxyfylline has anti-inflammatory activity and may function as a purinergic agonist via an adenosine receptor on the surface of the infiltrating neutrophil which can inhibit NADPH oxidase and apoptosis. This oral therapy can be continued, along with lifestyle changes, as maintenance therapy to prevent re-initiation and relapse.

Example 3

Patient is a 44 year old female who has had ulcerative colitis since 1994. It started with bleeding. She actually had bleeding and cramping about every six months. Each episode abated spontaneously without therapy. They began to increase in intensity until 2003.

In October 2003 patient had a colonoscopy and for the first time, an official diagnosis of ulcerative colitis was made. She was started on ASACOL (Medeva Pharma Schweiz AG, Switzerland) but still had recurrences; however, the recurrences were shorter. The recurrences occurred every 3-5 months. Some of the episodes were severe but did not respond to hydrocortisone enemas. Subsequently, she had a very severe episode that did not respond to ASACOL or the enemas. She was treated with prednisone and improved for a few months but then it recurred and was more severe than ever.

Flexible sigmoidoscopy showed moderately active diseases to exactly 20 cm (see FIGS. 1A-1E). Above that, the mucosa was normal and stool was normal. Biopsies and pictures were taken. Biopsy specimens showed diffuse colitis with distortion of crypt architecture, mononuclear cell expansion of the lamina propria, basal plasmacytosis and mucosal ulceration, consistent with chronic ulcerative colitis, severe activity, with epithelial changes negative for dysplasia. CMV was not identified.

Following sigmoidoscopy, patient was started on a once daily enema treatment with an enema formulation of the present invention comprising: 1) 40 cc of Rowasa (2.6 gms) (Mesalamine) Rectal Suspension; 2) 5 cc sodium cromolyn (100 mg/5 cc oral concentrate); 3) 15 cc of 1 Molar sodium butyrate (15 millimoles or 1.5 gms); and 4) 1 cc sodium budesonide (5 mg/cc). The patient also was started on oral R-dihydro lipoic acid 300 mg given twice daily.

After completion of 7 days of treatment, patient claims to be 85% improved having noticed improvement beginning about the fourth day. She is having no more cramping, no mucus, and no blood. Her stools are forming. Patient will continue for another week on treatment and then will be examined by sigmoidoscopy.

Figure 2B:
FIGS. 2A-2C show sigmoidoscopy results: distal sigmoid (FIG. 2A); rectum (FIG. 2B), and rectum (FIG. 2C) corresponding to Example 3.
Figure 2C:
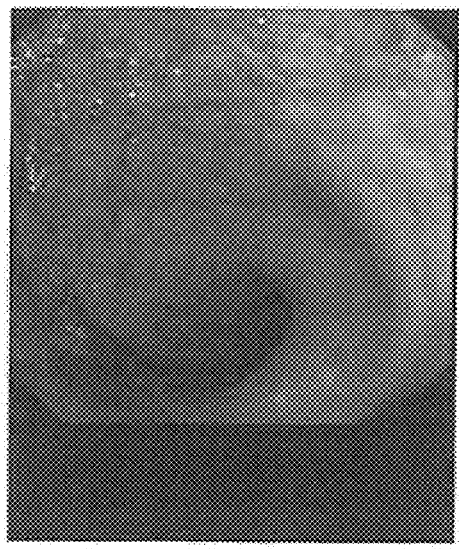
Figure 2A:
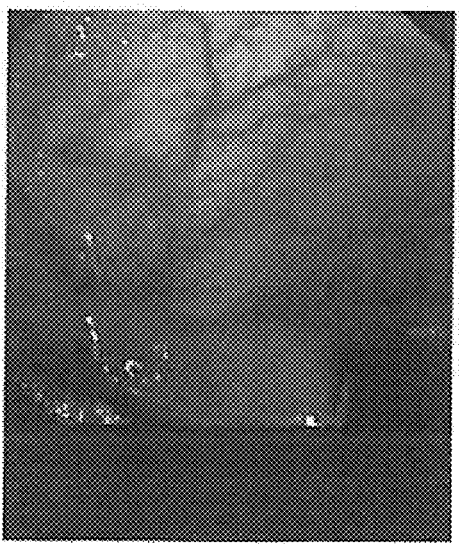

Flexible sigmoidoscopy of patient showed an absolutely normal looking mucus membrane (see FIGS. 2A-2C). Biopsies were taken. Biopsy specimens showed distortion of crypt architecture and minor mononuclear cell expansion of the lamina propria consistent with quiescent chronic ulcerative colitis. Active inflammation was not identified. The epithelial changes were negative for dysplasia.

Example 4

33 patients with distal ulcerative colitis were divided into two groups. For the first 23 patients treated, concomitant medications were allowed. A second group of 10 patients were treated for whom all ulcerative colitis related medications were stopped prior to treatment. In all cases, the patients were failing their usual therapy prior to treatment. For a few of these patients, these treatments were the last alternative prior to referral for colectomy.

An enema was prepared having a volume of 60 ml including 2.67 g of mesalamine, 5 mg of budesonide, 100 mg of sodium cromolyn, and 15 millimoles of sodium butyrate. The patients were instructed to administer the enema prior to going to bed, and to retain the contents of the enema overnight, or for at least four hours. Patients also took two 150-mg capsules of R-DHLA twice daily, for a total of 600 mg of R-DHLA daily.

Clinical evaluations including ulcerative colitis Mayo scoring and histology occurred at baseline and after 21 and 42 days of continuous treatment.

Group 1 (n=23) Patients with No Change in Concomitant Medication

Patients in Group 1 continued on their UC medications, which included mesalamine, steroids, immunomodulators and biologics.

Group 1 (n=23) Demographics:

| Patients | 23 |
|---|---|
| Male | 43% |
| Female | 57% |
| Age | |
| Mean | 45.4 |
| Min | 26.0 |
| Max | 72.0 |

-continued

| | |
|---|---|
| Ethnicity | |
| White | 95% |
| Black | 5% |
| Duration of UC, yrs | 1.5-27 |
| Pre-Treatment Mayo Score | |
| Mean | 8.6 |
| Minimum | 3.0 |
| Maximum | 12.0 |
| Pre-Treatment UC Therapies | |
| 5-ASA (oral or rectal) | 82% |
| Steroids (oral or rectal) | 41% |
| Immunomodulators (6-MP, AZA) | 18% |
| Biologics (Remicade, Humira) | 18% |

The mean ulcerative colitis Mayo Score for incoming patients in Group 1 was 8.6. Thus, even with treatment with conventional therapies, patients in Group 1 exhibited moderate to severe disease.

Group 1 (n=23) Extent of Exposure:

| # enemas dispensed per patient | |
|---|---|
| average | 122 |
| max | 440 |
| min | 15 |
| median | 42 |
| total | 2805 |

On average, patients were dispensed 122 enemas, providing approximately 17 weeks of daily treatment. Many patients stayed on the therapy for an additional period of time after the completion of six week study.

Group 1 (n=23) Efficacy Results—Mayo Scores:

Ulcerative colitis Mayo score results are shown in the tables below.

| Week | 0 | 3 | 6 |
|---|---|---|---|
| n | 22 | 22 | 20 |
| Average Mayo Score | 8.64 | 0.95 | 0.35 |
| Maximum Mayo Score | 12 | 4 | 4 |
| Minimum Mayo Score | 3 | 0 | 0 |

| Week | 3 | 6 |
|---|---|---|
| n | 22 | 20 |
| Patients with clinical response (Mayo score decreases ≥3) | 100% | 100% |
| Patients in clinical remission (Mayo score ≤2) | 82% | 95% |

As can be seen by the data above, all of the patients had a clinical response to the treatment after three weeks. Additionally, 19 out of 20 patients (95%) were in clinical remission after six weeks of treatment.

Group 1 (n=23) Efficacy Results—Histology Scores:
The histology results are shown in the following tables:

| | Week 0 | Week 3 | Week 6 |
|---|---|---|---|
| n | 21 | 22 | 14 |
| Average Histology Score | 3.05 | 0.14 | 0.36 |
| Maximum Histology Score | 5 | 1 | 4 |
| Minimum Histology Score | 1 | 0 | 0 |

| | Week 0 | Week 3 | Week 6 |
|---|---|---|---|
| Histological remission (0 score on histology): | 0% (n = 21) | 85% (n = 22) | 92% (n = 14) |
| Complete histological remission (Mayo ≤2 and Endoscopy ≤1 and Histology = 0) | 0% (n = 18) | 75% (n = 20) | 92% (n = 13) |

As can be seen by the data above, 13 out of 14 patients were in histological remission after six weeks of treatment. Additionally, 12 out of 13 patients were in were in complete histological remission after six weeks of treatment.

Group 2—Patients without Concomitant Medications (10 Patients)

In this second group, prior to initiation of the study, all concomitant ulcerative colitis medications were stopped.

Group 2 (n=10) Demographics:

| | |
|---|---|
| Patients | 10 |
| Male | 40% |
| Female | 60% |
| Age | |
| Mean | 45.0 |
| Min | 34.0 |
| Max | 62.0 |
| Ethnicity | |
| White | 100% |
| Black | 0% |
| Duration of UC, yrs | 0.3-23 |
| Pre-Treatment Mayo Score | |
| Mean | 7.6 |
| Minimum | 5.0 |
| Maximum | 9.0 |
| Pre-Treatment UC Therapies | |
| 5-ASA (oral or rectal) | 80% |
| Steroids (oral or rectal) | 30% |
| Immunomodulators (6-MP, AZA) | 0% |
| Biologics (Remicade, Humira) | 0% |

The patients in Group 2 all had the following characteristics: a baseline Mayo score of 5-9, disease extending less than 50 cm, and an ability to retain an enema.

Group 2 (n=10) Extent of Exposure:

| # enemas dispensed per patient | |
|---|---|
| average | 59 |
| max | 90 |
| min | 30 |
| median | 60 |
| total | 594 |

On average, patients were dispensed 59 enemas, providing approximately 8 weeks of daily treatment. Many patients stayed on the therapy for an additional period of time after the completion of six week study.

Group 2 (n=10) Efficacy Results—Mayo Scores:

Ulcerative colitis Mayo score results are shown in the tables below.

| Week | 0 | 3 | 6 |
|---|---|---|---|
| n | 10 | 10 | 10 |
| Average Mayo Score | 7.60 | 0.60 | 0.10 |
| Maximum Mayo Score | 9 | 3 | 1 |
| Minimum Mayo Score | 5 | 0 | 0 |

| Week | 3 | 6 |
|---|---|---|
| n | 10 | 10 |
| Patients with clinical response (Mayo score decreases ≥3) | 100% | 100% |
| Patients in clinical remission (Mayo score ≤2) | 90% | 100% |

As can be seen by the data above, all of the patients had a clinical response to the treatment after three weeks. Additionally, all of the patients were in clinical remission after six weeks of treatment, and 9 out of 10 patients were in clinical remission after three weeks.

Group 2 (n=10) Efficacy Results—Histology Scores:
The histology results are shown in the following tables:

| | Week 0 | Week 3 | Week 6 |
|---|---|---|---|
| n | 10 | 10 | 10 |
| Average Histology Score | 2.30 | 0.20 | 0.00 |
| Maximum Histology Score | 3 | 2 | 0 |
| Minimum Histology Score | 1 | 0 | 0 |

| | Week 0 | Week 3 | Week 6 |
|---|---|---|---|
| n | 10 | 10 | 10 |
| Histological remission (0 score on histology): | 0% | 90% | 100% |
| Complete histological remission (Mayo ≤2 and Endoscopy ≤1 and Histology = 0): | 0% | 90% | 100% |

As can be seen by the data above, all of the patients were in histological remission after six weeks of treatment, and 9 out of 10 patients were in histological remission after three weeks of treatment. Additionally, all of the patients were in were in histological remission after six weeks of treatment, and 9 out of 10 patients were in were in histological remission after three weeks of treatment.

Efficacy Results as a Function of Baseline Mayo Score for Combined Groups 1 and 2

Using the following definition of mild, moderate, and severe disease, the percentage of patients in clinical remission (Mayo score≤2), histological remission (histology score=0) and complete histological remission (Mayo score≤2 and Mayo endoscopy subscore≤1 and histology score=0) are compared as a function of disease severity.

| At Baseline | | | At Week 3 | | | At Week 6 | | |
|---|---|---|---|---|---|---|---|---|
| | Mayo score | n | % in clinical remission | % in histological remission | % in complete histological remission | % in clinical remission | % in histological remission | % in complete histological remission |
| mild | 0-4 | 2 | 100% | 100% | 100% | 100% | 100% | 100% |
| moderate | 5-8 | 22 | 91% | 91% | 86% | 100% | 100% | 100% |
| severe | 9-12 | 8 | 63% | 75% | 50% | 86% | 67% | 80% |

As shown above, 100% of mild-moderate UC patients were in complete histological remission at week 6, as were 80% of severe UC patients. Regardless of UC severity at baseline, patients responded to treatment, including 86% of severe patients in clinical remission and 80% of severe patients in complete histological remission. The data demonstrates that the therapy would be effective over the entire range of UC disease severity.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A method of treating ulcerative colitis in a mammal requiring such treatment, comprising administering to said mammal:
   a) orally, at least once daily, from about 100 mg to about 1000 mg of R-dihydro-lipoic acid and pharmaceutically acceptable salts thereof; and
   b) rectally an enema comprising:
      i) from about 500 mg to about 5000 mg of 5 ASA;
      ii) from about 0.5 mg to about 10 mg of budesonide;
      iii) from about 10 to about 1000 mg of cromolyn sodium; and
      iv) from about 5 ml to about 50 ml of a 1 molar short chain fatty acid solution, wherein the short chain fatty acid is sodium butyrate; and
   c) allowing the contents of the enema to be retained for at least about 4 hours.

2. The method of claim 1, wherein the enema is administered at about bedtime.

3. The method of claim 1, wherein the enema is retained for at least about 5 hours.

4. The method of claim 1, wherein the amount of 5-ASA is from about 750 mg to about 3000 mg.

5. The method of claim 3, wherein the amount of 5-ASA is about 2.7 g.

6. The method of claim 1, wherein the amount of budesonide is from about 1 mg to about 5 mg.

7. The method of claim 1, wherein the amount of cromolyn sodium is about 100 mg.

8. The method of claim 1, wherein the amount of sodium butyrate is about 15 ml of a 1 molar solution.

9. The method of claim 1, wherein the amount of R-dihydro-lipoic acid is from about 150 mg to about 750 mg.

10. The method of claim 1, wherein the amount of R-dihydro-lipoic acid is from about 300 mg to about 600 mg.

11. The method of claim 1, wherein the volume of the enema administered is from about 40 ml to about 80 ml.

12. The method of claim 1, wherein the amount of R-dihydro-lipoic acid is about 600 mg; the amount of 5-ASA is about 2.67 g; the amount of budesonide is about 5 mg; the amount of cromolyn sodium is about 100 mg; and the amount of sodium butyrate is about 15 ml of a 1 molar solution.

13. A method of claim 1, wherein the enema is administered once daily for about six weeks, and about twice weekly thereafter.

14. A method of decreasing an ulcerative colitis Mayo Score in a mammal in need of such treatment, comprising:
- a) determining the ulcerative colitis Mayo Score of a mammal in need of treatment;
- b) administering to said mammal:
  - i) orally, at least once daily, from about 100 mg to about 1000 mg of R-dihydro-lipoic acid and pharmaceutically acceptable salts thereof; and
  - ii) rectally an enema comprising:
    - from about 500 mg to about 5000 mg of 5 ASA;
    - from about 0.5 mg to about 10 mg of;
    - from about 10 to about 1000 mg of cromolyn sodium; and
    - from about 5 ml to about 50 ml of a 1 molar solution of sodium butyrate;
  - iii) allowing the contents of the enema to be retained for at least about 4 hours;
- c) repeating said daily administering step b) until a decrease in the ulcerative colitis Mayo Score of ≥3 is observed.

15. The method of claim 14, wherein the decrease in the ulcerative colitis Mayo Score is observed after about three to six weeks.

\* \* \* \* \*